(12) United States Patent
Lee et al.

(10) Patent No.: US 7,223,412 B1
(45) Date of Patent: May 29, 2007

(54) STAPHYLOCOCCAL ENTEROTOXIN SEC-SER, EXPRESSION VECTOR AND HOST CELL, PRODUCTION METHOD THEREOF, AND MANUFACTURING METHOD OF VACCINE

(75) Inventors: Hong-Kyun Lee, Taejeon (KR); Yong-Ho Park, Seoul (KR); Kyu-Boem Han, Taejeon (KR); Byoung-Sun Chang, Taejeon (KR); Yong-Jun Lee, Seoul (KR)

(73) Assignee: LG Chem-Investment Ltd., Seoul (KR)

( * ) Notice: Subject to any disclaimer, the term of this patent is extended or adjusted under 35 U.S.C. 154(b) by 712 days.

(21) Appl. No.: 10/203,536

(22) PCT Filed: Oct. 31, 2000

(86) PCT No.: PCT/KR00/01241

§ 371 (c)(1),
(2), (4) Date: Aug. 12, 2002

(87) PCT Pub. No.: WO01/60851

PCT Pub. Date: Aug. 23, 2001

(30) Foreign Application Priority Data

Feb. 17, 2000 (KR) .................................. 2000-7612

(51) Int. Cl.
*A61K 39/02* (2006.01)
*A61K 39/085* (2006.01)
*A61K 39/00* (2006.01)
*C12N 15/00* (2006.01)
*C12N 15/09* (2006.01)
*C07H 21/04* (2006.01)
*C07K 1/00* (2006.01)

(52) U.S. Cl. ................. 424/236.1; 424/190.1; 424/234.1; 424/184.1; 424/243.1; 424/832; 530/350; 530/825; 435/320.1; 435/69.3; 536/23.7

(58) Field of Classification Search ................ 530/350, 530/825, 402; 536/23.7; 514/2; 435/480, 435/320.1, 71.1, 69.3; 424/190.1, 200.1, 424/234.1, 236.1, 832, 184.1, 243.1
See application file for complete search history.

(56) References Cited

OTHER PUBLICATIONS

Houghten et al. Vaccines86, Cold Spring Harbor Laboratory, p. 21-25, 1986.*
Marcy L. Hoffmann et al., "Predictions of T-Cell Receptor- and Major Histocompatibility Complex-Binding Sites on Staphylococcal Enterotoxin C1", Infection and Immunity, Aug. 1994, vol. 62, No. 8, pp. 3396-3407.
Gregory A. Bohach et al., "Nucleotide sequence of the staphylococcal enterotoxin C1 gene and relatedness to other pyrogenic toxins", Molecular General Genetics, (1987).
Terence N. Turner et al., "Residues 20, 22 and 26 Determine the Subtype Specificities of Staphylococcal Enterotoxins C1 and C2", Infection and Immunity, Feb. 1992, vol. 60, No. 2, pp. 694-697.
C.J. Hovde et al., Molecular Biology, vol. 13, No. 4, pp. 897-909, No. 4 (1994).
KK. Pulling et al., Abstracts of the 91$^{st}$ General Meeting of the American Society for Microbiology, vol. 9, pp. 71 (1991).
G.A. Bohach et al., Natural Toxins 2, pp. 131-154, pp. 143-147 (1996).
W.A. Ferens et al., Infect-Immun-, vol. 66, pp. 573-580, vol. 66, No. 2 (1998).

* cited by examiner

*Primary Examiner*—S. Devi
(74) *Attorney, Agent, or Firm*—Birch, Stewart, Kolasch & Birch, LLP

(57) ABSTRACT

The present invention relates to a method of producing recombinant modified Staphylococcal toxin having improved stability, comprising the steps of preparing a modified toxin in which a specific amino acid sequence is substituted and a vector for expressing the modified toxin, and culturing *E. coli* transformed with the vector, and a use thereof for the vaccine.

6 Claims, 26 Drawing Sheets

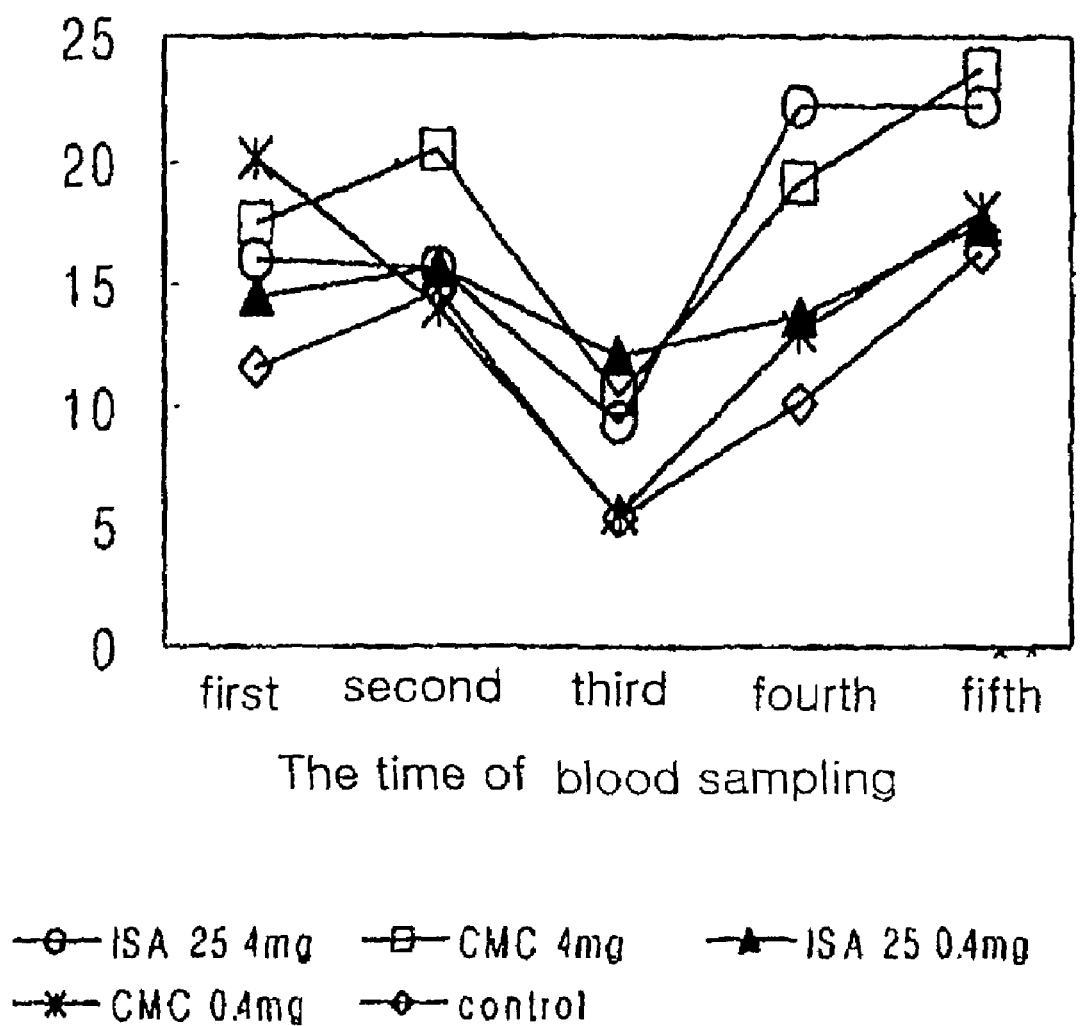

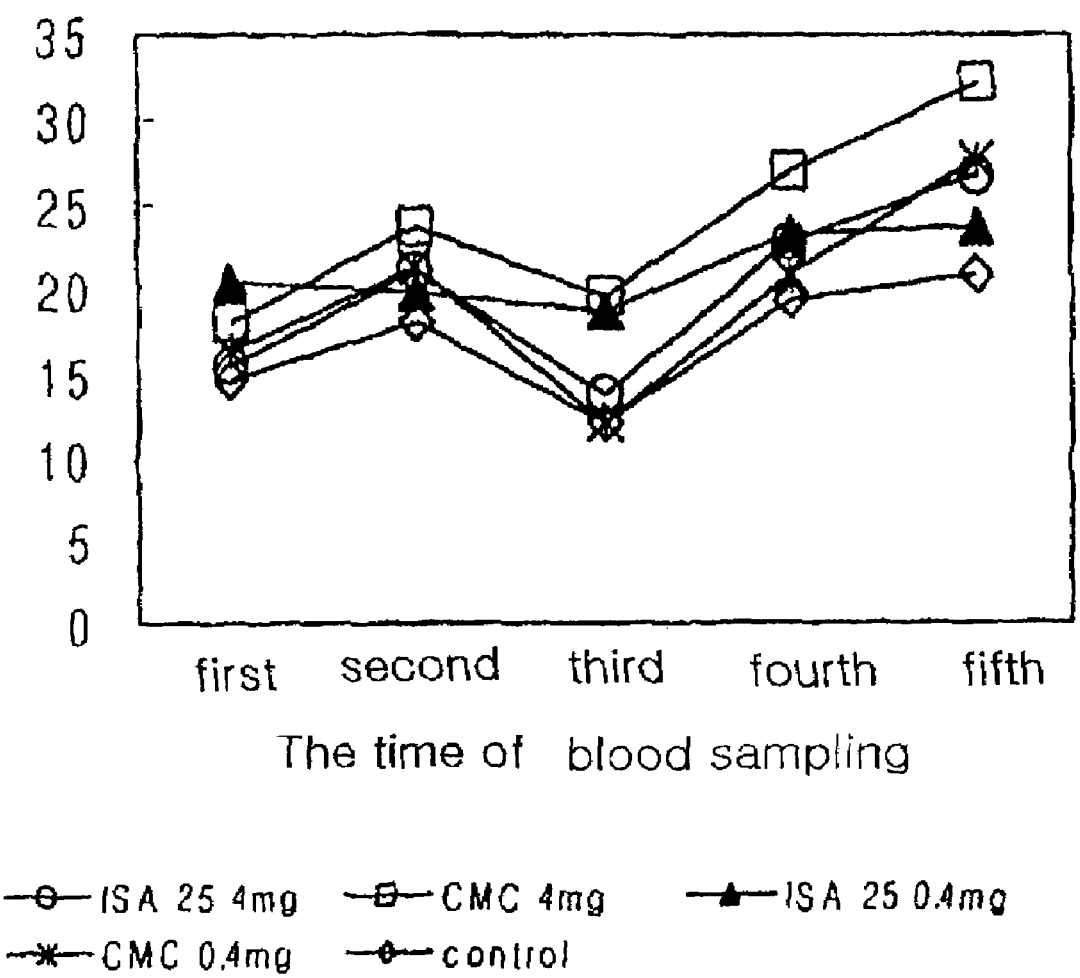

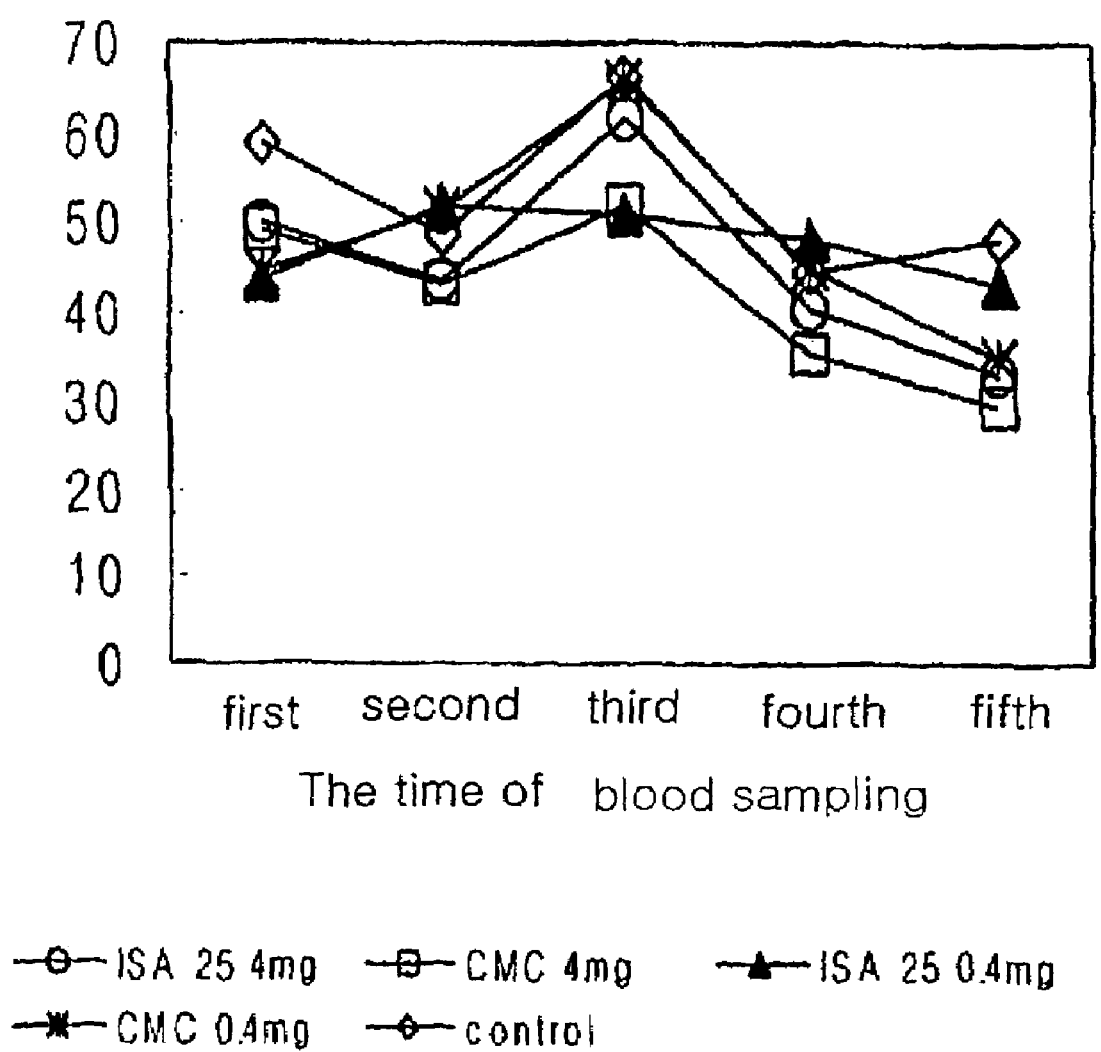

STAPHYLOCOCCAL ENTEROTOXIN SEC-SER, EXPRESSION VECTOR AND HOST CELL, PRODUCTION METHOD THEREOF, AND MANUFACTURING METHOD OF VACCINE

This application is the national phase under 35 U.S.C. § 371 of PCT International Application No. PCT/KR00/01241 which has an International filing date of Oct. 31, 2000, which designated the United States of America.

BACKGROUND OF THE INVENTION (a) Field of the Invention

The present invention relates to a method for stabilizing a modified protein of SEC1 (Staphylococcal enterotoxin C1) that is one of the Staphylococcal enterotoxins, and a method for producing the same in large quantity. More particularly, the present invention relates to a method of increasing stability of a modified toxin by substituting one cysteine group in an amino acid sequence of modified toxin protein with a serine group to inhibit the dimer formation.

(b) Description of the Related Art

Generally, Staphylococcal enterotoxin (SE) is a pyrogenic toxin (hereafter referred to as "PT"). This kind of toxin is typically produced by *Staphylococcus aureus* and *Staphylococcus pyrogens*, although they have been found to be produced in the cells of mammals or pathogenic bacteria and viruses. Staphylococcal PT includes SE types (A, B, C1, C2, C3, D, E, G, H), Staphylococcal pyrogenic exotoxins (SPE) A and B, toxic shock syndrome toxin (TSST-1), etc.

Streptococcal PT includes SPE A, B, C, mitogenic factor (MF) and Streptococcal super antigen (SSA). These are exoproteins and are found in Streptococci of the B, C, F and G groups. All toxins pertaining to PT are proteins of monomers and have a molecular weight of approximately 22–28 kDa, and they are very similar in their amino acid sequences. They are divided into three groups according to the homology of the amino acid sequences. The first group includes SE type B (SEB), SE type C (SEC), SPE type A (SPEA), SSA, etc. and they are 49% or more identical in their sequences. The second group is 84% or more identical in their sequences and SE type A (SEA), SE type E (SEE), SE type D (SED), SPE type C (SPEC) are of this group. The third group has a low sequence homology, and TSST-1, SPEB and PSET belong to this group. Amino acid sequences are versatile but many of the sequences showing homology are concentrated on four loci. These loci are believed to relate to common biological activities of toxins. Such common biological activities include pyrogenicity, immune response suppression, cytokine induction, proliferation of lymphocytes, superantigenicity, etc. Such biological activity plays an important role in lethal diseases such as TSS (toxin shock syndrome). In addition, a unique biological activity of SE is inducing diseases such as vomiting, diarrhea and food poisoning. The characteristics of SE that distinguish them from other PTs are sulfide bonds forming disulfide loop structures. If the amino acid sequence of these functional structures are deleted or substituted with other amino acid sequence, SE can be used as vaccines or treating agents in humans or animals.

The present invention relates to the production of a modified Staphylococcal toxin C1 for the above-mentioned purpose, and a method for stabilizing said modified toxin. The genetic sequence of modified Staphylococcal toxin C1 (SEC1) was found by Gregory A, Bohach et al. (Molecular General Genetics (1987) 209: 15–20), and then the functional structural locus of SEC1 was found from amino acid primary sequence as a result of continuous studies of Dr. Bohach et al. (Terence N. Turner et al. (1992), Infection and Immunity 60(2): 694–697, Carolyn J. Hovde et al (1994), Molecular Microbiology 13(5): 897–909, Marcy L. Hoffman et al (1994), Infection and Immunity 62(8): 3396–3407).

Then, Bohach G. A et al. prepared a modified protein (SEC1-12) by deleting amino acid sequence 94 to 106 and combining an amino acid sequence at the deleted portion. The amino acid sequence 94 to 106 is a loop portion wherein SEC1 exhibits most functions as a superantigen. Thus, the prepared modified toxin can function as a mitogen in which most biological activities are removed, and thus it can function as a vaccine which elicits non-specific cellular immune responses as well as forms antibodies for humoral immune responses The present inventor transferred said genes to an *E. coli* expression vector in order to produce a toxin protein in a large quantity to obtain recombinant modified toxin therefrom. However, there was a problem in that the formation of multiple structures due to the disulfide bonds largely increased by an odd number of cysteines in modified protein.

In order to solve these problems, the present inventors largely improved the stability of a modified protein toxin by substituting cysteine groups that cause the formation of dimer with serine groups, and successfully completed the process for preparing large quantities of modified toxin C1 whose host is *E. Coli*.

Accordingly, it is an object of the present invention to provide a process for preparing a Staphylococcal modified toxin C1 in a large quantity by transforming *E. coli* with the modified toxin whose amino acid sequence is substituted by the amino acid sequence which inhibits the formation of multiple structures, and a use thereof in a vaccine for preventing, alleviating or treating mastitis in cows.

SUMMARY OF THE INVENTION

In order to achieve said object, the present invention provides a modified Staphylococcal toxin SEC-SER which is characterized in that the 95th amino acid, cysteine, in a modified Staphylococcal toxin C1 is substituted with serine.

The present invention also provides genes coding a polypeptide of modified Staphylococcal toxin SEC-SER.

The present invention also provides a ptrp 3H SEC-SER expression vector containing the genes coding the polypeptide of modified Staphylococcal toxin SEC-SER.

The present invention also provides a host cell that is transformed with said expression vector.

Said host cell is preferably bacteria, and more preferably, *E. coli*.

The present invention also provides a method for producing a SEC-SER polypeptide of a modified toxin having stability, comprising the step of substituting the $95^{th}$ amino acid, cysteine, in modified Staphylococcal toxin C1 with serine.

The present invention also provides a method for separating and purifying recombinant modified toxin SEC-SER, comprising the step of culturing *E. coli* that is transformed so that the recombinant modified Staphylococcal toxin SEC-SER is expressed therein, and then fractionally precipitating the expressed protein with ammonium sulfate and passing it through cation exchange column chromatography.

The concentration of said ammonium sulfate is preferably 0 to 4 M. In addition, said cation exchange resin preferably has cation exchange functional groups attached thereto such as CM (carboxymethyl) and SP (sulphopropyl).

In addition, the method of the present invention comprises the step of passing through anion exchange column chromatography or hydrophobic column chromatography before or after the step of passing through cation exchange column chromatography. Said anion exchange resin preferably has anion exchange functional groups attached thereto such as DEAE (diethylamino ethyl), Q (quaternary ammonium), QAE (quaternary aminoethyl), etc. Said hydrophobic resin preferably has hydrophobic boding functional groups attached thereto such as phenyl, butyl and octyl.

The present invention also provides a method for manufacturing vaccine from the recombinant modified Staphylococcal toxin SEC-SER.

Said vaccine is preferably administrated into animals including cows, pigs, horses, sheep, hens, dogs, cats, etc. Said vaccine is used for preventing or treating infectious disease of animals caused by microorganisms. Said vaccine is preferably used for preventing and/or treating mastitis in animals, and more preferably, mastitis in cows.

BRIEF DESCRIPTION OF THE DRAWINGS

FIGS. 8A to 8G show the change of immune cells in cows.

DETAILED DESCRIPTION AND THE PREFERRED EMBODIMENTS

The present invention will now be explained in more detail.

Figure 1:
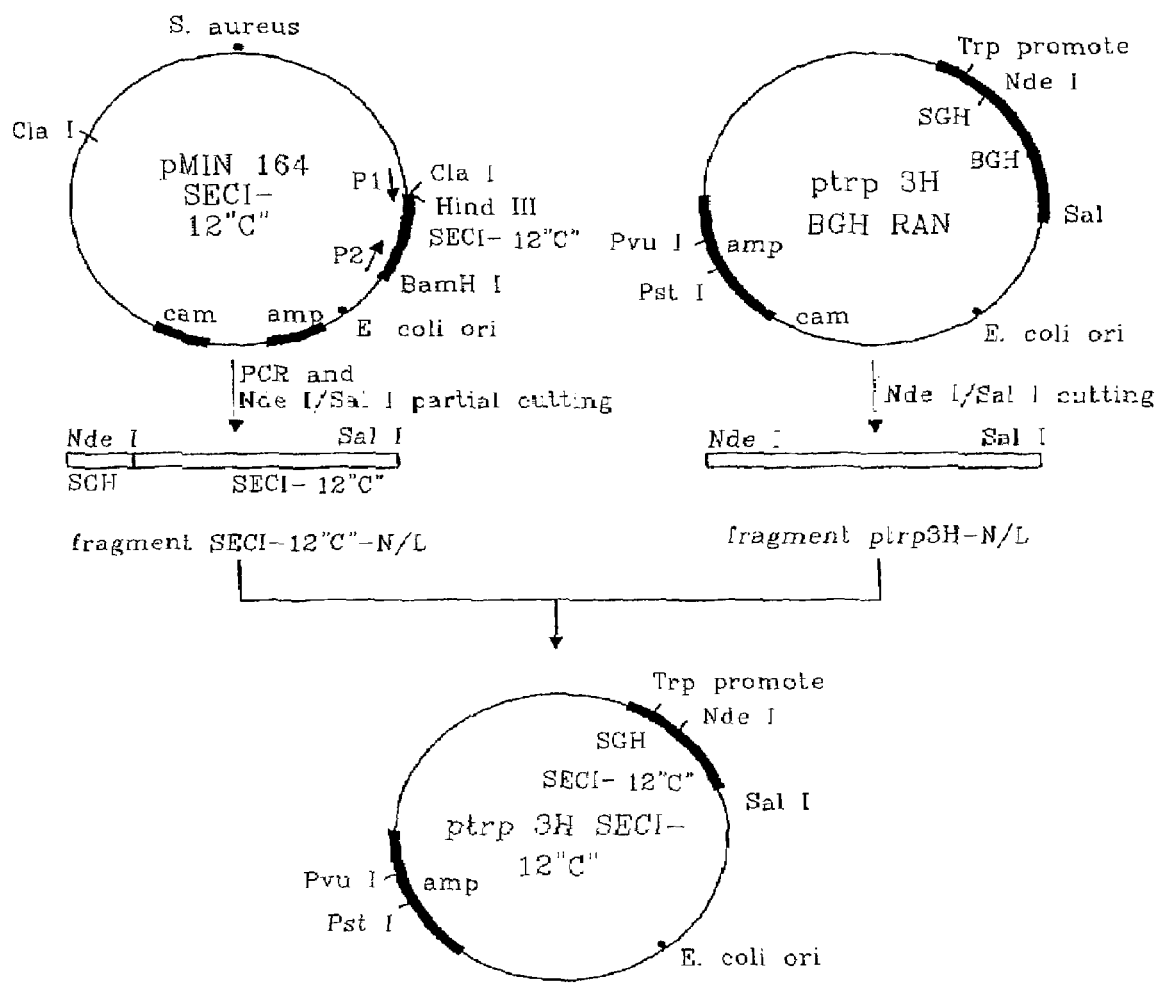
FIG. 1 shows a method for producing an *E. coli* expression vector containing the genes of modified Staphylococcal toxin.

In the present invention, cysteine codon in a SEC1-12" C" gene was substituted with serine codon by a polymerase chain reaction (PCR) of a pMIN 164 SEC1-12" C" containing a modified Staphylococcal protein (SEC1-12" C") as provided by Dr. Bohach, and SEC1-12" C" was resynthesized such that the recognition sites for NdeI, SalI restriction enzymes were produced in both ends, and then it was inserted between the NdeI and SalI recognition sites of the expression vector ptrp 3H BGHRAN whose host is *E. coli* (See FIG. 1). In the polymerase chain reaction, a primer, which is designed so that the partial sequence of SGH is linked when synthesizing mRNA in *E coli* to induce a high expression at the interpretation thereof, was synthesized and used as 5'-terminal of genes. Preferably, the 5'-terminal includes the following nucleic acid sequence:

Primer 1 (P1) (SEQ ID NO: 3) 5'-GGAATTCCATATGATC-GAAAATCAGCGTTTATTCAACATTGCAGTTTCTA GCATGGAGGAATTATAAATGGAGAGC-CAACCAGACCCTAC-3'

The 5'-terminal of said primer has a NdeI recognition site, and includes the SGH partial sequence for inducing high expression, and, after stop codon, has start codon again and has a 5'-terminal amino acid sequence of SEC1-12" C" gene again.

The 3'-terminal was designed so that the SalI recognition site is located at the end of the SEC1-12"C" gene, and preferably, includes the following sequence:

Primer 2 (P2) (SEQ ID NO: 4) 5'-GAATTGTCGACTTATC-GATTCTTTGTTGTAAG-3'

The genes, which were PCR-amplified using primers P1 and P2, and using pMIN164 SEC-12" C" vector containing SEC1-12"C" genes as a template, was treated with restriction enzymes NdeI and SalI to make fragments. The expression vector was also treated with NdeI and SalI, and the expression vector was ligated with said amplified genes. Then, *E. coli* was transformed with said expression vector to obtain ptrp 3H SGH SEC1-12"C" plasmid.

However, the present invention continuously proceeds in order to substitute some of the amino acid sequence with amino acid sequence inhibiting the formation of multiple structures in the modified protein SEC1-12"C". Specifically, in order to substitute the cysteine codon that was substituted for the firstly removed site in SGH SEC1-12"C" with serine codon, the following primers P3 and P4 were designed:

Primer 3 (P3) (SEQ ID NO: 5) 5'-AATTACTATGTAAACT-GCTCTGGCAAAACT-3'

Primer 4 (P4) (SEQ ID NO: 6) 5'-GTTTTGCCAGAG-CAGTTTACATA-3'

As a result of amplifying a part of the genes using primers P1 and P4 and conducting a polymerase chain reaction using ptrp 3H SGH SEC1-12"C" as a template, a fragment 380 bp in size was obtained. As a result of amplifying another part of the genes using primers P3 and P2 and conducting a polymerase chain reaction using ptrp 3H SGH SEC1-12"C" as a template, a fragment 410 bp in size was obtained. As a result of PCR amplification using said two fragments as template and using primers P1 and P2, a complete modified genes 780 bp in size was obtained.

Since the restriction enzyme NdeI recognition site exists at the 5'-terminal and at the 565 base location in said gene fragment, said fragment was incompletely treated with NdeI and treated again with SalI to prepare a SEC-SER gene fragment having a serine codon instead of a cysteine codon. Said modified gene fragment was inserted between the NdeI and SalI recognition sites of ptrp 3H BGHRAN, and *E. coli* was transformed therewith to obtain ptrp 3H SGH SEC-SER plasmid (See FIG. 2). Said *E. coli* was cultured in an appropriate medium, and then the expressed SEC1-SER modified protein was separated and purified. Said *E. coli* was shake-cultured in M9 medium to the extent that O.D. amounts were 0.5 to 0.8, and then a proper amount of IAA (Indole acrylic acid) was added thereto to induce the expression, and it was further shake-cultured for 6 hours or more.

According to the purpose, an aerobic culturing method can be used. Expressed modified toxin proteins are all soluble proteins, their amounts corresponds to 15% of total protein of E. coli, and an inclusion body was not observed therein. In order to separate E. coli from the medium, E. coli culturing liquid in which a modified toxin protein was expressed was separated with a continuous centrifuge, and precipitates were recovered. The recovered E. coli precipitates were suspended in a buffer solution for cell disruption, and were passed through a homogenizer or microfluidizer and disrupted to separate the soluble proteins. In order to separate insoluble material from cell disrupted solution, supernatant was recovered using the continuous centrifuge, and it was passed through an ultra-filtration membrane with a pore size of 300 kDa and then an ultra-filtration membrane with a pore size of 10 kDa. And then, in order to remove residual ions, diafiltration was performed by 10 kDa ultra-filtration. And it was repeated to lower the conductivity of the solution.

Although the purity can be increased by fractional precipitation using ammonium sulfate (1.6 M–3.0 M) before ultra filtration, this step can be omitted. The retentate that was concentrated by ultra filtration is passed through a cation exchange resin (CM or S-SEPHAROSE™) column that was equilibrated with an appropriate buffer solution, bound thereto, and washed with a buffer solution, and was then eluted using 100 mM of NaCl solution or eluted by concentration gradient of NaCl. Although proteins purified with cation exchange column chromatography can be passed through an anion exchange column in order to further remove E. coli derived material, this step can be omitted.

A protein solution purified with column chromatography was concentrated with an ultra-filtration membrane with a pore size of 10 kDa, and the buffer was exchanged with PBS (phosphate buffered saline). Although the exchange of buffer can be carried out by repeated dilution and concentration using PBS as a diluant for ultra-filtration, or it can be carried out by passing through a gel filtration column equilibrated with PBS, this step can be omitted according to the purpose. In order to use a purified modified toxin protein as a vaccine for mastitis in cows, tests regarding the selection of an appropriate amount of protein and adjuvant were conducted in test animals, and good immunogens were identified. Specifically, in the test on cows (Test 3), the distribution rates of monocyte that are involved in the initial defense mechanism and MHC class II molecules largely increased at the beginning after injection, and the rate of B lymphocyte that plays a critical role in humoral immune response (antibody production) remarkably increased and then returned to normal value after a certain time elapsed. In addition, the distribution rate of T lymphocytes from which the promotion of the cellular immune response (secondary immune response) can be indirectly recognized is confirmed to increase at the point when the primary immune response decreases, and thus it can be seen that effective immunization occurs after tertiary injection. The present invention will be explained in more detail with reference to the following Examples.

COMPARATIVE EXAMPLE

SEC1-12"C": The Amplification of Genes and the Preparation of Expression Vector

Step 1)

The following primer was synthesized from the base sequence information of already cloned SEC1 genes:

Primer 1 having the following sequence (P1) has the recognition site for NdeI that is a restriction enzyme in the expression vector ptrp 3H BGHRAN, includes the partial sequence of SGH, and, after stop codon, has start codon again and 36 base sequence which codes the 5'-terminal of SEC1 genes:

5'-GAATTCCATATGATCGAAAATCAGCGTT-TATTCAACATTGCAGTTTCTAG CATGGAGGAAT-TATAAATGGAGAGCCAACCAGACCCTAC-3' (SEQ.ID.NO: 3)

Primer 2 having the following sequence (P2) includes a recognition site for SalI that is a restriction enzyme in the expression vector ptrp 3H BGHRAN, and has a 17 base sequence which codes the 3'-terminal of SEC 1 genes:

5'-GAATTGTCGACTTATCGATTCTTTGTTGTAAG-3' (SEQ.ID.NO: 4)

Step 2)

1 ng of shuttle vector pMIN164 SEC1-12"C" was introduced in the reaction tube as a template, and primers P1 and P2 prepared in step 1 were introduced therein such that they amount to 10 pmole, and then 10 μl of 2 mM dNTP (2 mM dGTP, 2 mM dCTP, 2 mM dATP, 2 mM dTTP), Tag polymerase and distillated water were added thereto such that the total volume amounted to 100 μl. 25 cycles of polymerase chain reactions were conducted under conditions of denaturation at 95° C. for 1 minute, annealing at 55° C. for 40 seconds and polymerization at 72° C. for 2 minutes.

The thus obtained PCR product was separated in 7% polyacrylamide gel and it was identified that approximately 780 bp of DNA was amplified. Then, the product was separated and purified from said polyacrylamide gel. The obtained fragment will be referred to as SEC1-12"C" hereafter.

Step 3)

2 μg of plasmid ptrp 3H BGHRAN were completely cut using the restriction enzymes NdeI and SalI in buffer solution D from Poscochem Company (6 mM Tris-HCl, 6 mM $MgCl_2$, 150 mM NaCl, 1 mM DTT), and then it was separated with 0.7% agarose gel to separate and purify 2.4 kb of fragment. Said fragment will be referred to as ptrp 3H-N/L hereafter.

The SEC1-12"C" fragment obtained in step 2 was treated with NdeI and SalI, but it was incompletely cut and was extracted with phenol/chloroform and dissolved in 20 μl of TE solution. It was separated with 7% polyacrylamide gel to separate and purify approximately 770 bp fragment. Said fragment will be referred to as SEC1-12"C"-N/L. The obtained fragments were ligated in the following manner: 100 ng of fragment ptrp 3H-N/L, 100 ng of fragment SEC1-12"C"-N/L, 3 μl of 10-fold ligation buffer, and 10 units of T4 DNA ligase were introduced in a ligation reaction tube, and distillated water was added thereto such that the total volume amounted to 20 μl, and then a ligation reaction was conducted for 6 hours at 16° C. After completing the reaction, *E. coli* W3110 (ATCC 37339) was transformed with the ligation reaction product to obtain expression vector ptrp 3H SEC1-12"C" containing the fragment SEC1-12"C" (See FIG. 1).

EXAMPLE 1

The Preparation of Modified Genes in which Cysteine Codon is Substituted with Serine Codon Step 1)

In order to substitute cysteine codon that was substituted for SEC1-12"C" genes with serine codon again, the following primers were synthesized.

The primer having the following base sequence (P3) contains the base sequence of SEC1-12"C" wherein cysteine codon in 5'→3' direction (sense codon) is substituted with serine codon:

5'-AATTACTATGTAAACTGCTCTGGCAAAACT-3' (SEQ.ID.NO: 5)

The primer having the following base sequence (P4) contains the base sequence of SEC1-12"C" genes wherein cysteine codon in 3'→5' direction (antisense codon) is substituted with serine codon:

5'-GTTTTGCCAGAGCAGTTTACATA-3' (SEQ.ID.NO: 6)

Primes P3 and P4 include complementary base sequence.

Step 2)

11 ng of ptrp 3H SEC1-12"C" were introduced in the reaction tube 1 as a template, and primers P3 and P4 were introduced therein such that they amounted to 10 pmole. 1 ng of said template was introduced in the reaction tube 2, and primers P2 and P3 were introduced therein in an amount of 10 pmole, respectively. A 10-fold polymerization buffer, 2 mM dNTP, Tag polymerase and distillated water were introduced in the reaction tubes 1 and 2, respectively, and a polymerase chain reaction was conducted in the same manner as in Comparative Example.

Thus obtained PCR products were separated in 7% polyacrylamide gel, and it was identified that 380 bp and 410 bp of DNA were amplified in the reaction tubes 1 and 2, respectively.

Step 3)

Both DNA's amplified in step 2 were introduced in the reaction tube as a template in an amount of 1 ng, respectively, and the prepared primers P1 and P2 were added thereto such that they amounted to 10 pmole. A 10-fold polymerization buffer, 2 mM dNTP, Tag polymerase and distillated water were introduced in the reaction tube, and a polymerase chain reaction was conducted in the same manner as step 2. The obtained PCR product was separated in 7% polyacrylamide gel, and it was identified that 780 bp of DNA were amplified. Said fragment is referred to as SEC-SER.

Step 4)

The SEC-SER fragment was separated and purified in 7% polyacrylamide gel, and it was treated with NdeI and SalI but incompletely cut, and then it was extracted with phenol/chloroform and dissolved in 20 µl of TE solution. It was separated and purified with 7% polyacrylamide gel again to obtain approximately 770 bp of fragment. Said fragment is referred to as SEC-SER-N/L. The obtained fragment SEC-SER-N/L and the fragment ptrp 3H-N/L obtained in step 3 of Comparative Example were ligated and transformation was conducted in the same manner as step 3 of Comparative Example to obtain the expression vector ptrp 3H SEC-SER containing fragment SEC-SER-N/L (See FIG. 2).

EXAMPLE 2

The Inducement of Expression of SEC-SER Genes and the Identification of Base Sequence Step 1)

50 colonies of recombinant *E. coli* obtained in Example 1 were shake-cultured in a liquid Luria medium containing 50 µg/ml of ampicillin (6% bactotripton, 0.5% yeast extract, 1% NaCl) for 12 hours. Then, 3 ml of each colony were transferred to 300 ml of an M9 medium (40 Mm $K_2HPO_4$, 22 Mm $KH_2PO_4$, 8.5 mM NaCl, 18.7 mM $NH_4Cl$, 1% glucose, 0.1 mM $MgSO_4$, 0.1 mM $CaCl_2$, 0.4% casaminoic acid, 10 µg/ml vitamin B1, 40 µg/ml ampicillin), respectively, and were shake-cultured at 37° C. for 4 hours. When the absorbance of the bacteria culturing liquid reached approximately 0.5–0.8 at a wavelength of 650 nm, IAA (indole acrylic acid) was added thereto such that the final concentration amounted to 50 µg/ml. About 4 hours after adding IAA, the absorbance of the cell culturing liquid was measured, and then it was centrifuged using a centrifuge (Beckman J2-21, JA14 rotor) at 11,000 rpm for 25 minutes to recover bacterial cell precipitates. Electrophoresis on the recovered cell precipitates was conducted according to Laemmli's method (Laemmli, Nature 227:680(1970) in 15% polyacrylamide gel in the presence of SDS to identify the expression. Then, the clones that were expressed in an amount of about 15% compared to the control were selected.

*E. coli* that was transformed with the expression vector ptrp 3H SEC-SER was deposited at the Korean Bioengineering Laboratory Gene Source Center on 1999, 9, 2 under deposit No. KCTC 0645BP. The bacteriological characteristics of said strain is as follows: optimum pH 7.0–7.4, temperature 37° C., it can grow in nutrition source LB or an M9 medium, Gram negative. In order to identify the base sequence of said expression vector, DNA sequencing was conducted by a cycle sequencing method using an ABI prism 377 DNA sequencer (PerkinElmer Company). As a result, it can be identified that the part corresponding to the $95^{th}$ cysteine codon in the base sequence coding original SEC1-12"C" protein was substituted with serine codon.

EXAMPLE 3

The Purification of SEC-SER Modified Protein Expressed in *E. coli*

(The Culture and Recovery of *E. coli*, Cell-Disruption Step)

An *E. coli* host cell KCTC 0645BP that was designed to express a SEC-SER modified protein was shake-cultured with an M9 medium in a 30 L fermentation bath, and was recovered using a continuous centrifuge (LAPX 202BTG, Alpha-Labal Company), and then it was suspended in 4 L of a 10 mM tris buffer solution (pH 7.0). The suspension was passed through a microfluidizer (Microfluidics Corp., U.S.A.) under a pressure of 8,000 psi to disrupt the cell membrane of the *E. coli*, and supernatant was recovered using a continuous centrifuge.

(Fractional Precipitation Step and Ultra Filtration Step)

1.6 M of ammonium sulfate was added to said supernatant, and said mixture was dissolved at 4° C. to recover supernatant using a high speed centrifuge (J2-21M, BECKMAN). Then, ammonium sulfate was added again to said supernatant such that the final concentration of ammonium sulfate amounted to 3.5 M, said mixture was dissolved at 4° C., and then the precipitated layer was recovered using a centrifuge. Said precipitated layer was dissolved in 4 L of a 10 mM tris buffer solution (pH 6.5), it was passed through an ultra-filtration membrane with a pore size of 300 kDa to collect the filtrate, and was passed again through the ultra filtration membrane with a pore size of 10 kDa to concentrate the retentate. The retentate was repeatedly diluted and concentrated with a 10 mM Tris buffer solution (pH 6.5) to control the conductivity to less than 800 μmho.

(Column Chromatography and the Exchange of Buffer Solution)

Figure 3:
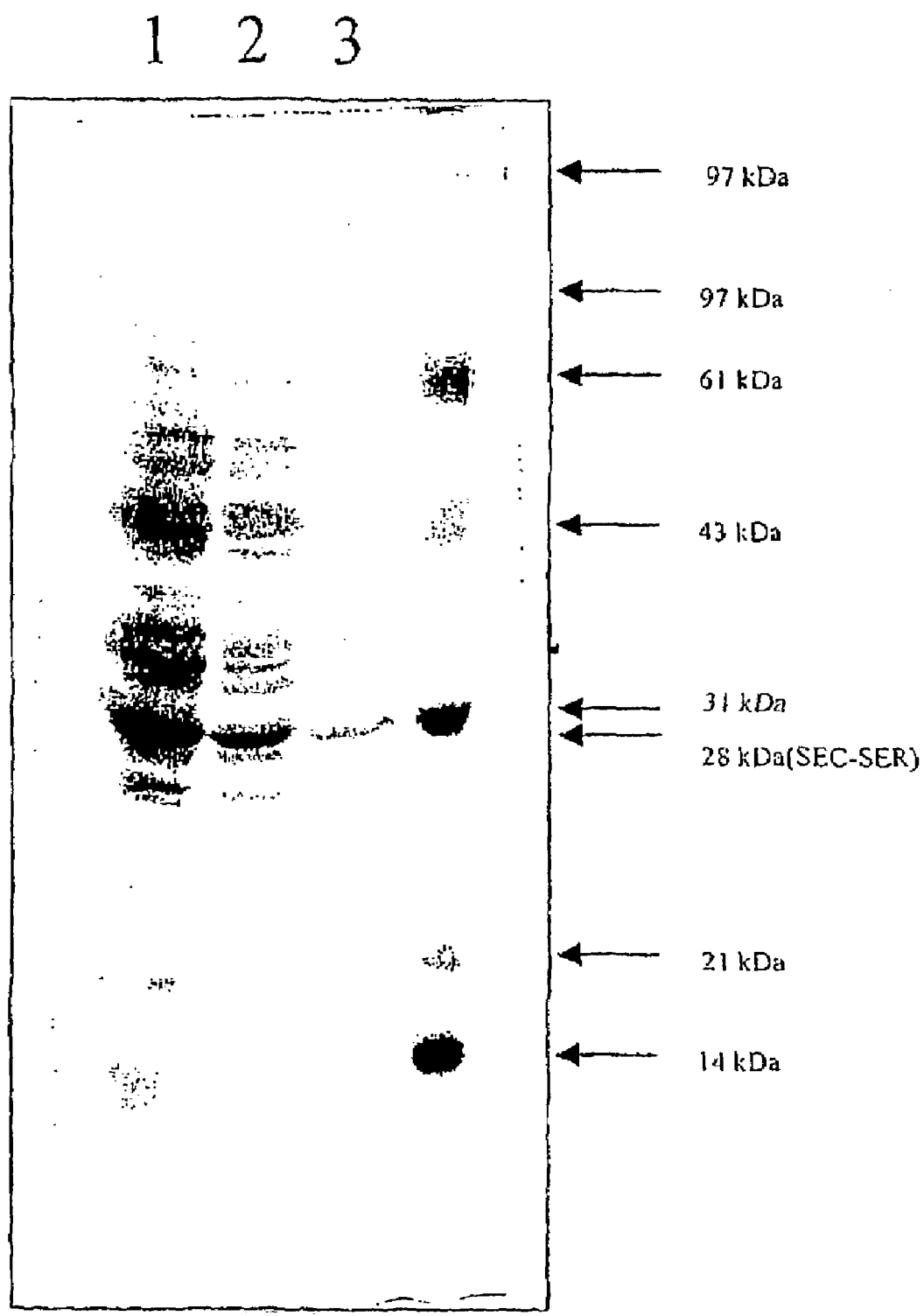
FIG. 3 shows a method for purifying the modified toxin expressed in *E. coli* with non-reducing SDS-PAGE.
Figure 4A:
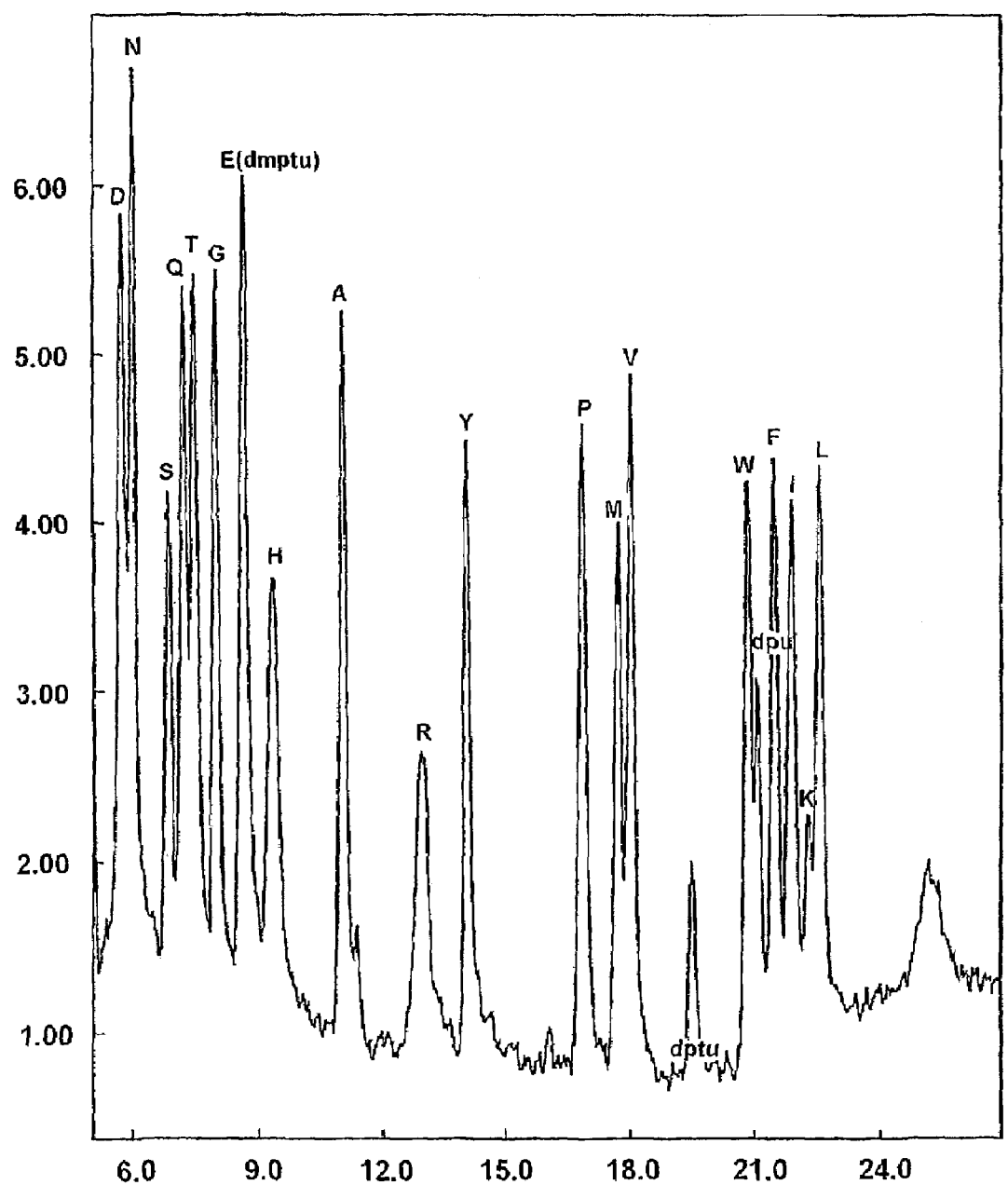
FIGS. 4A to 4K show the results of analyzing 10 amino acid sequence from the N-terminal of the purified modified toxin.
Figure 4B:
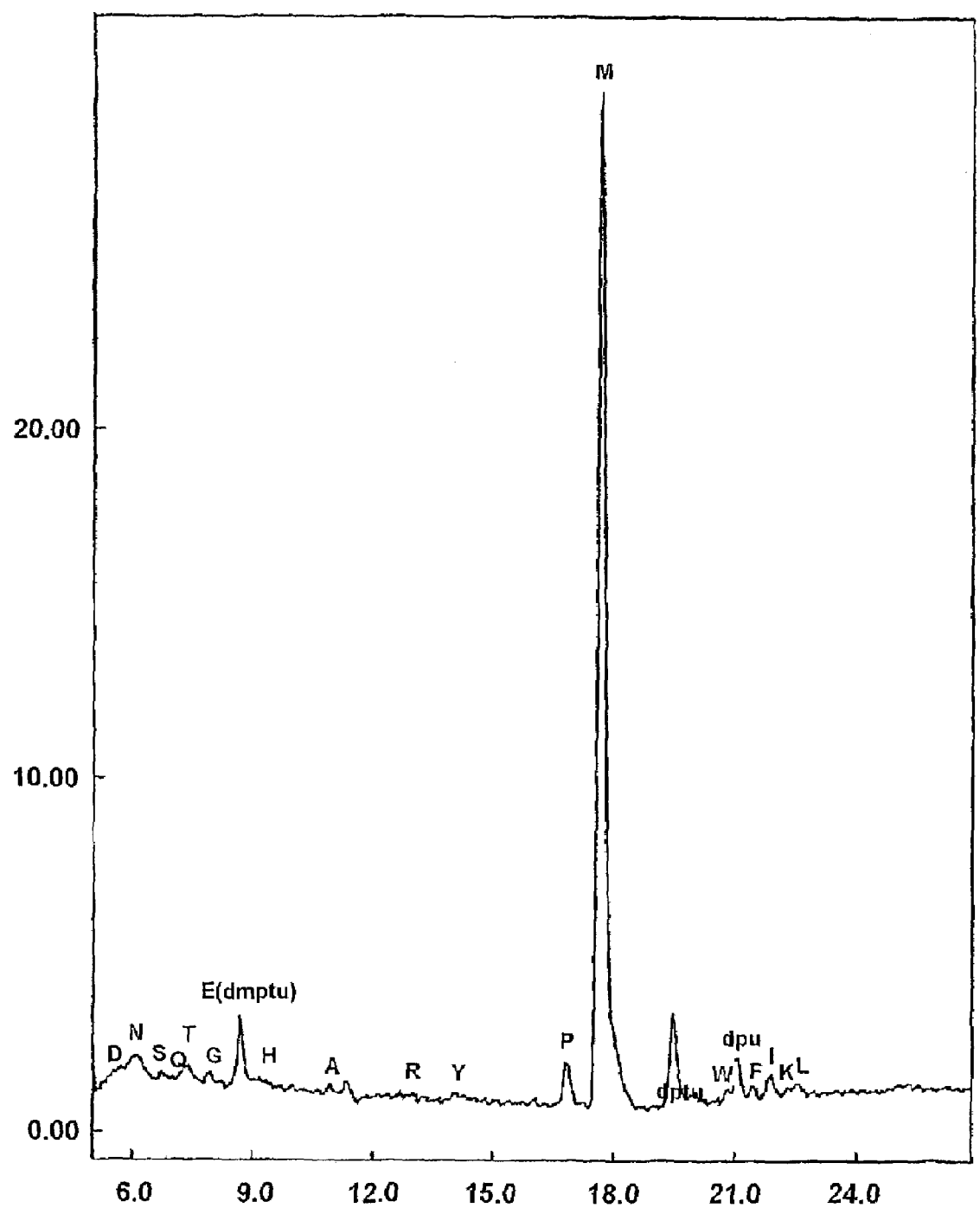
Figure 4C:
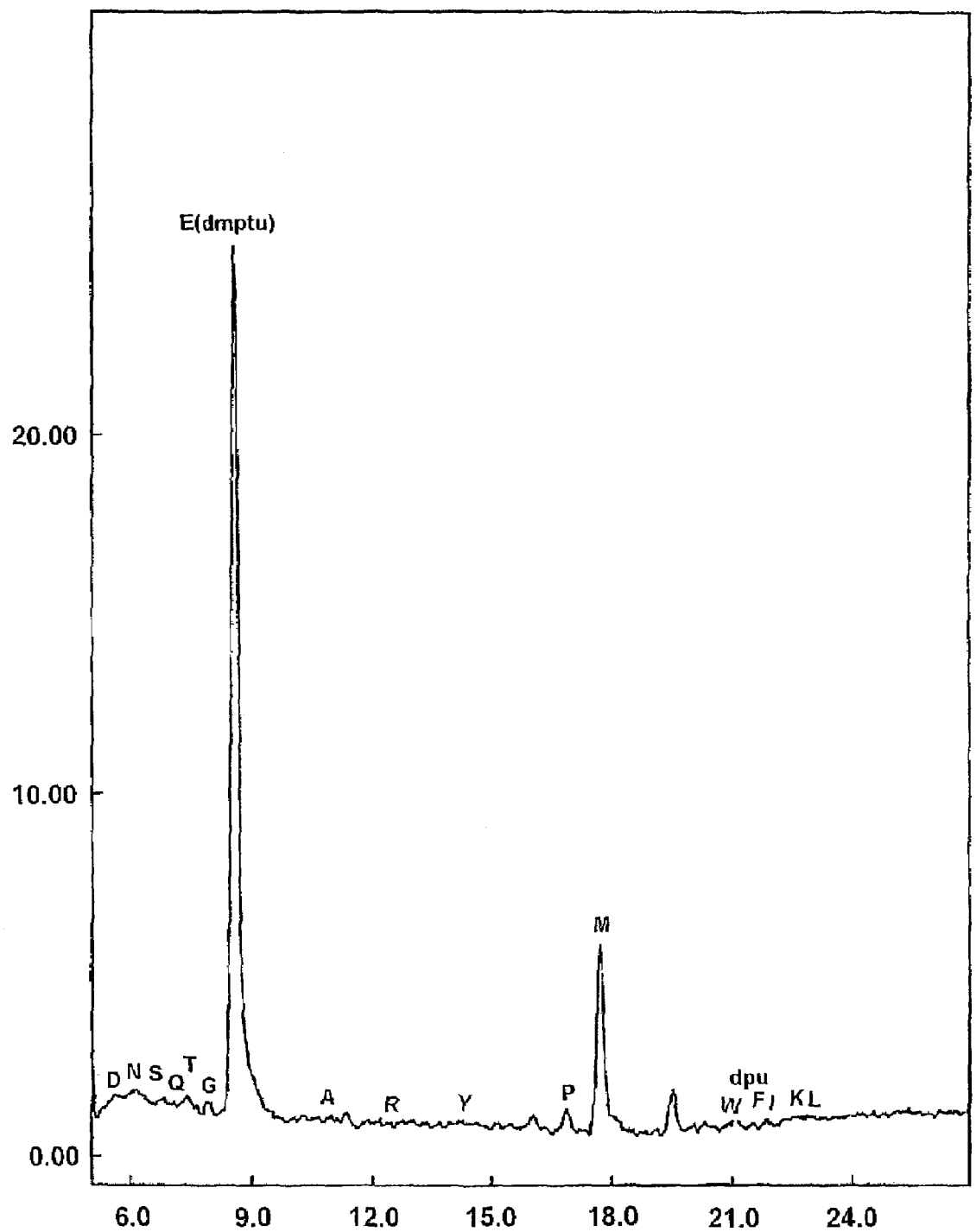
Figure 4D:
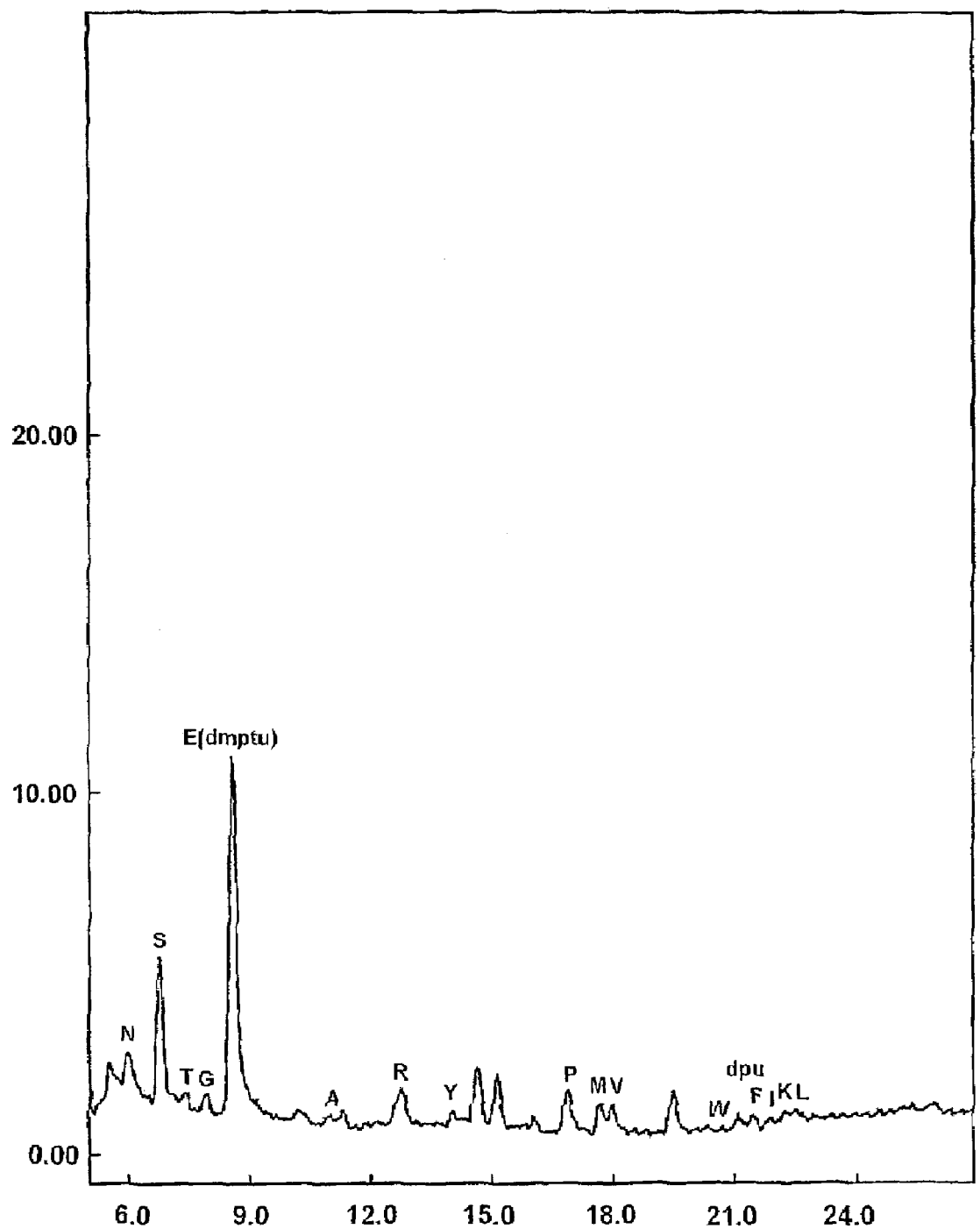
Figure 4E:
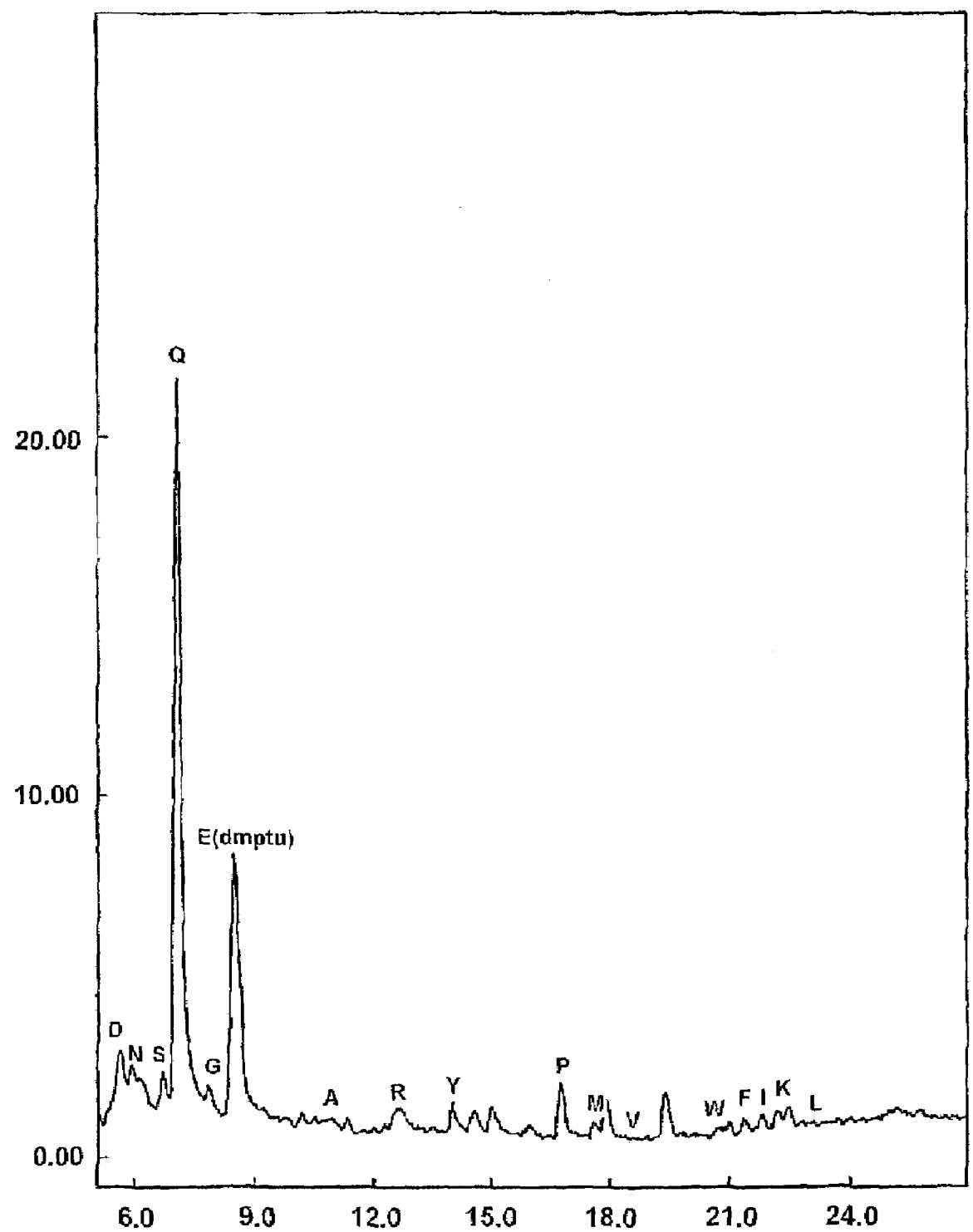
Figure 4F:
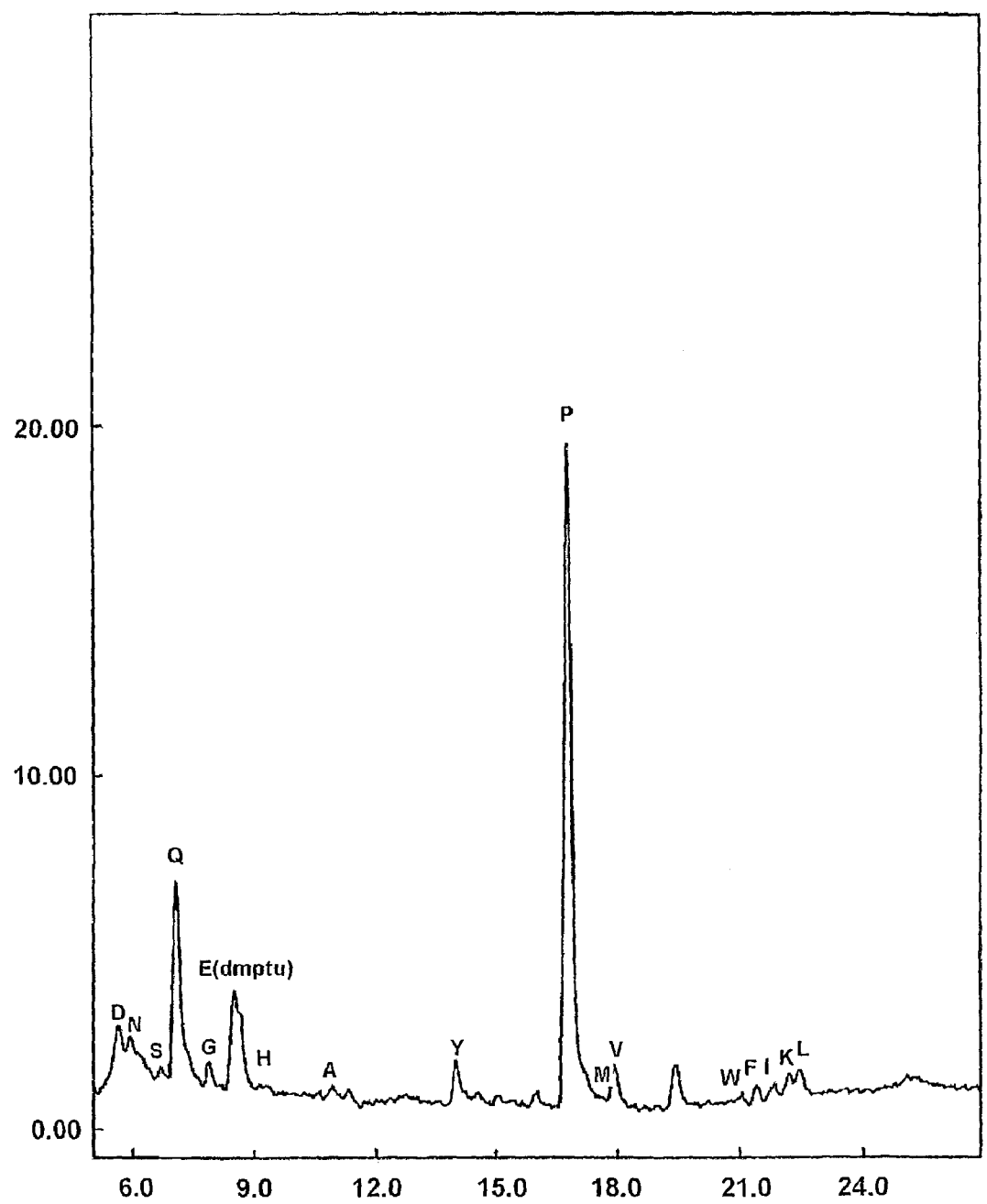
Figure 4G:
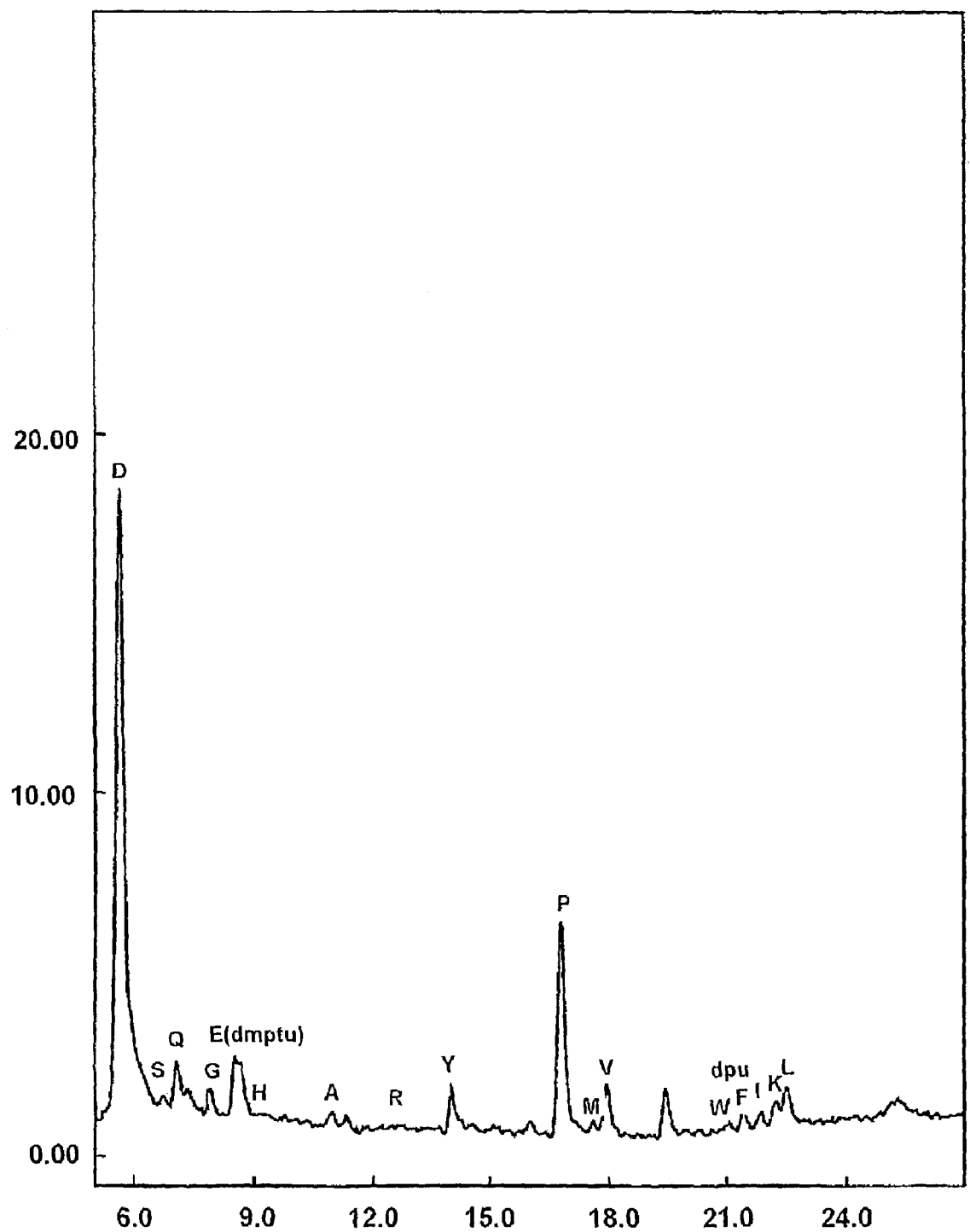
Figure 4H:
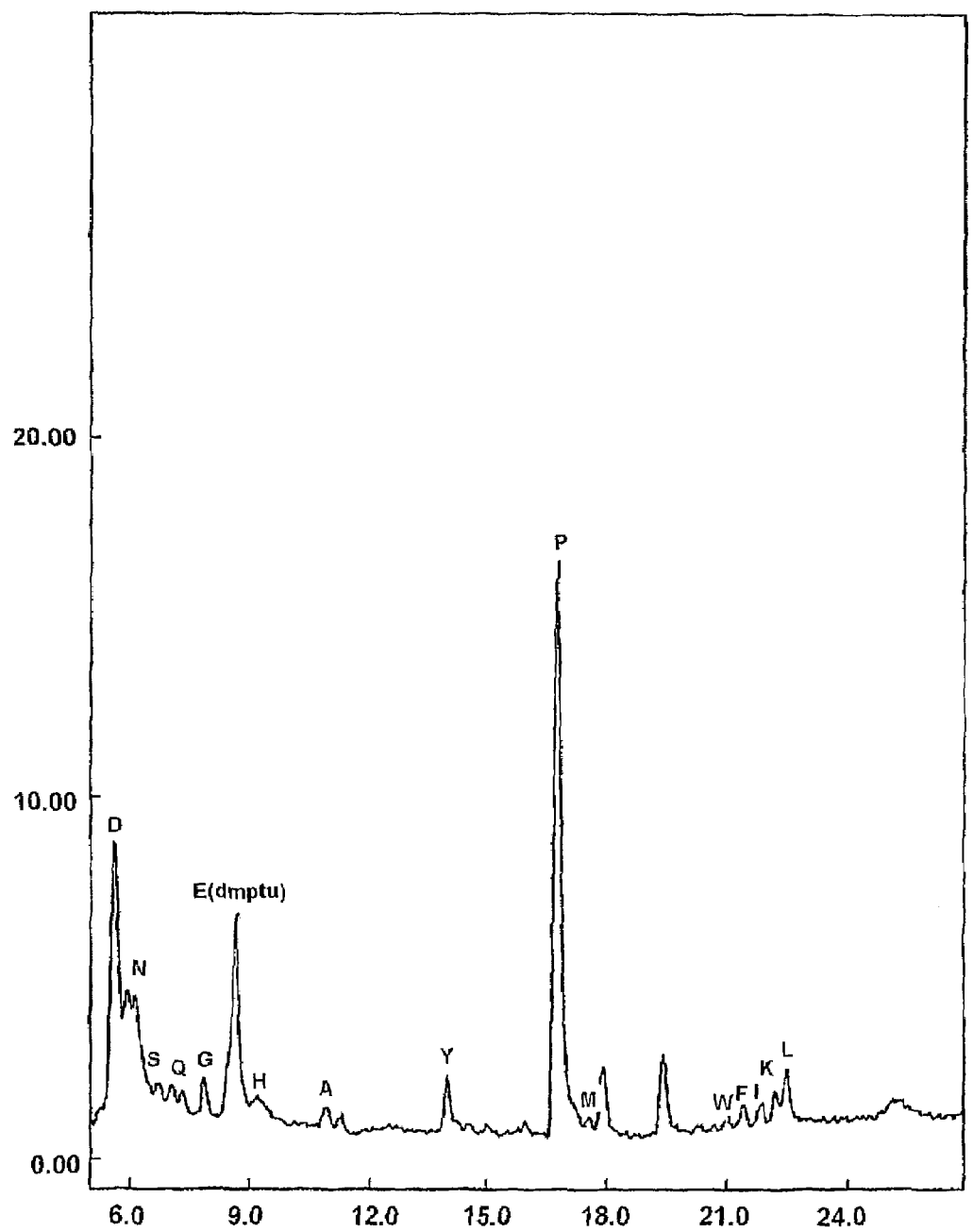
Figure 4I:
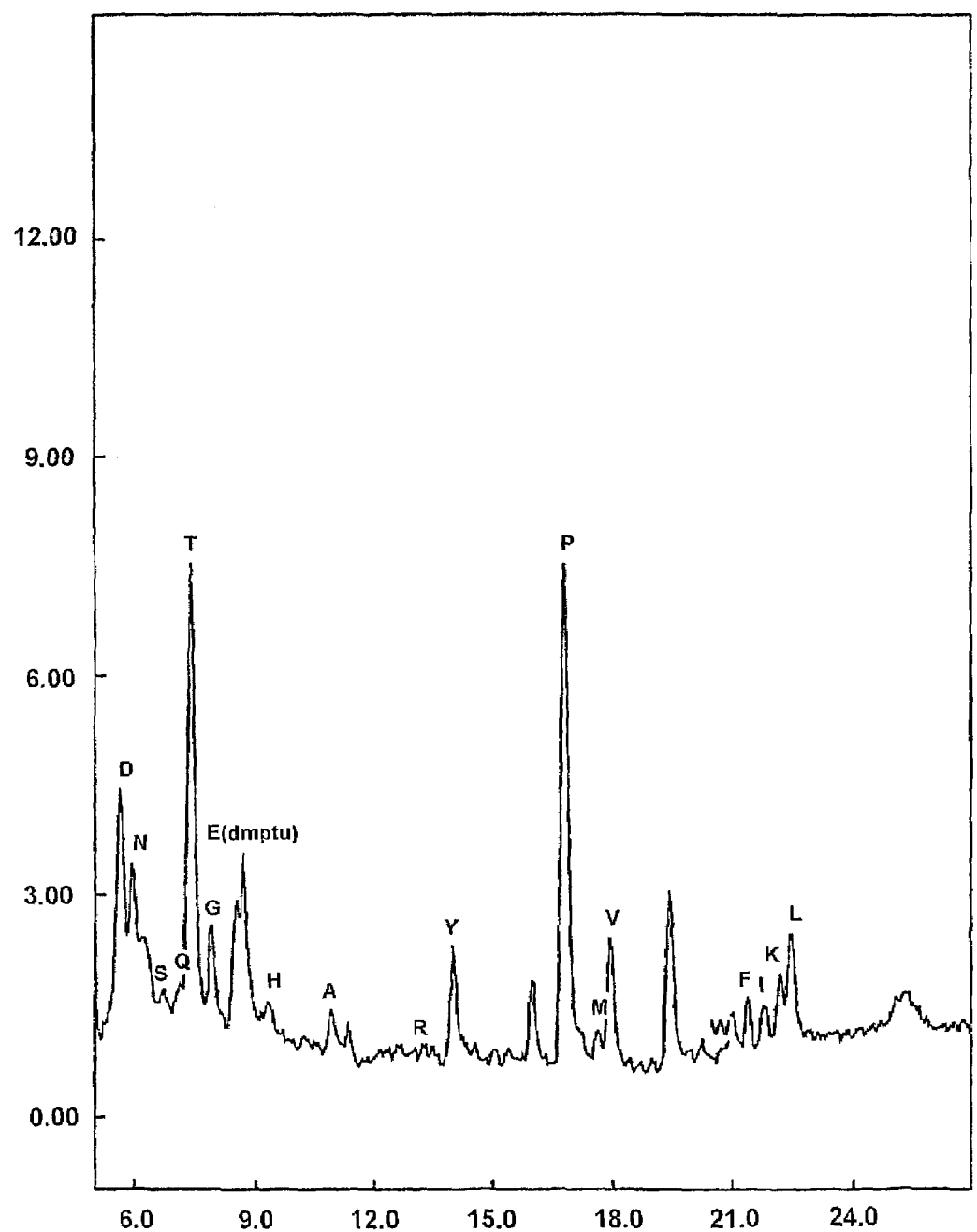
Figure 4J:
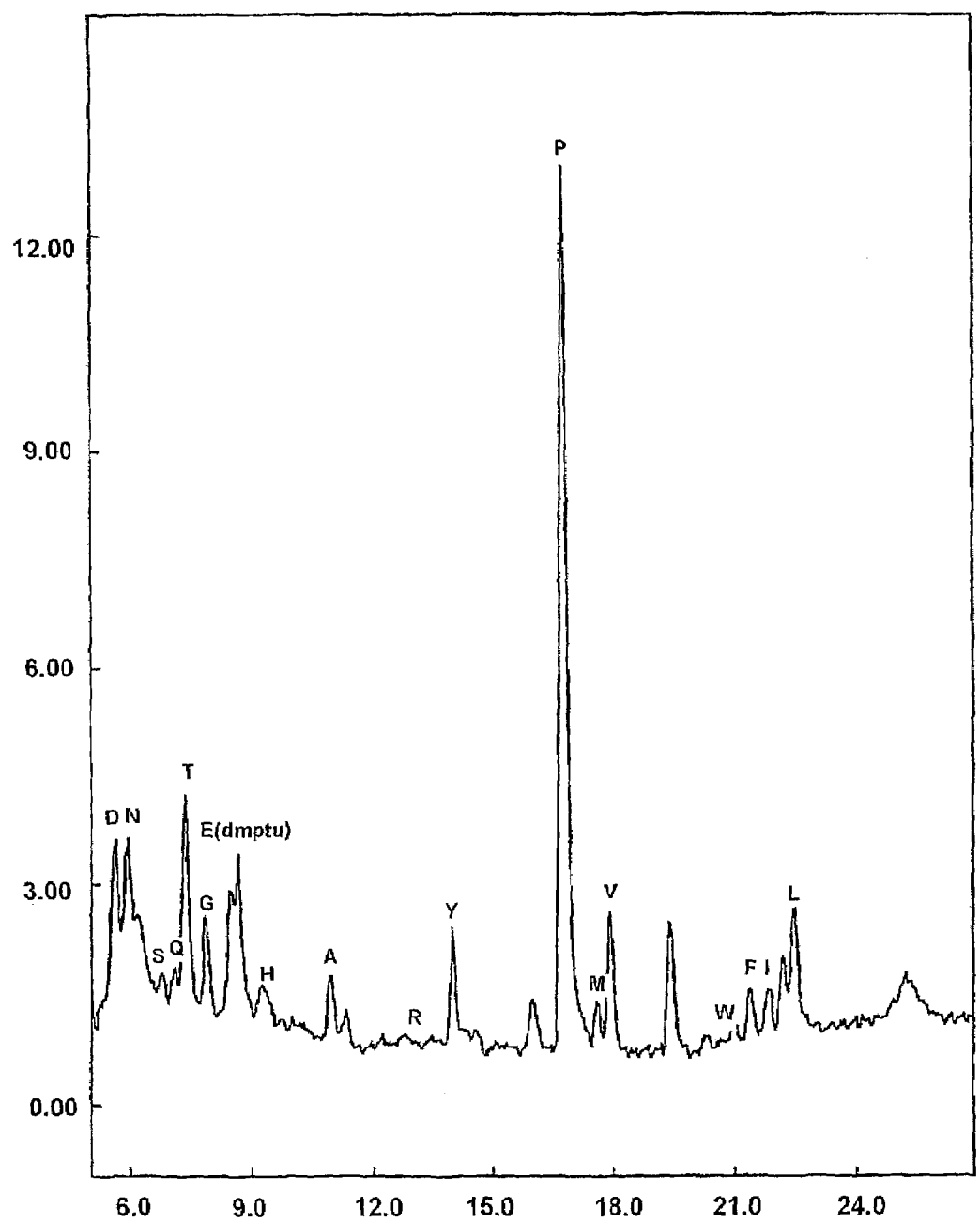
Figure 4K:
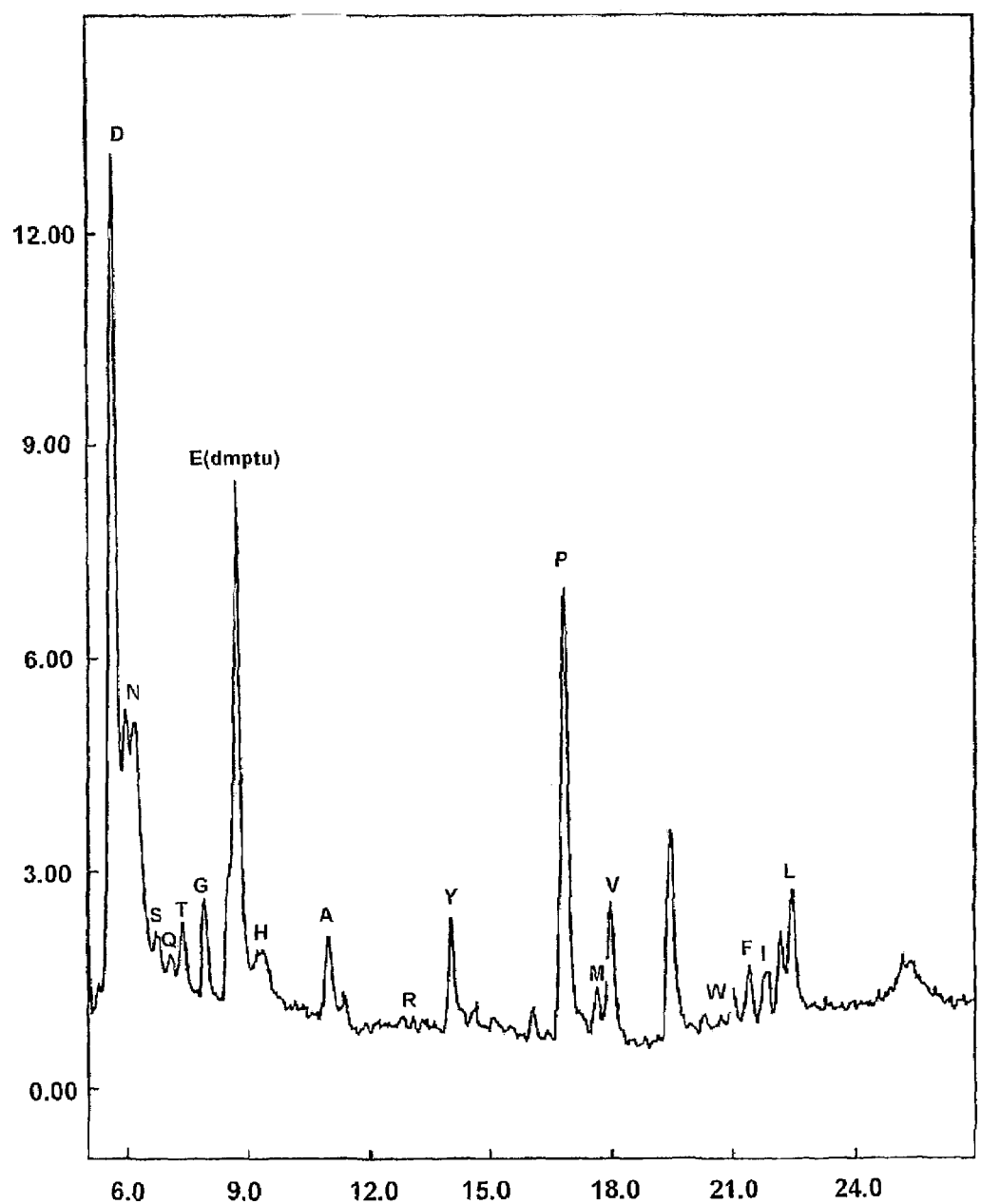
Figure 5:
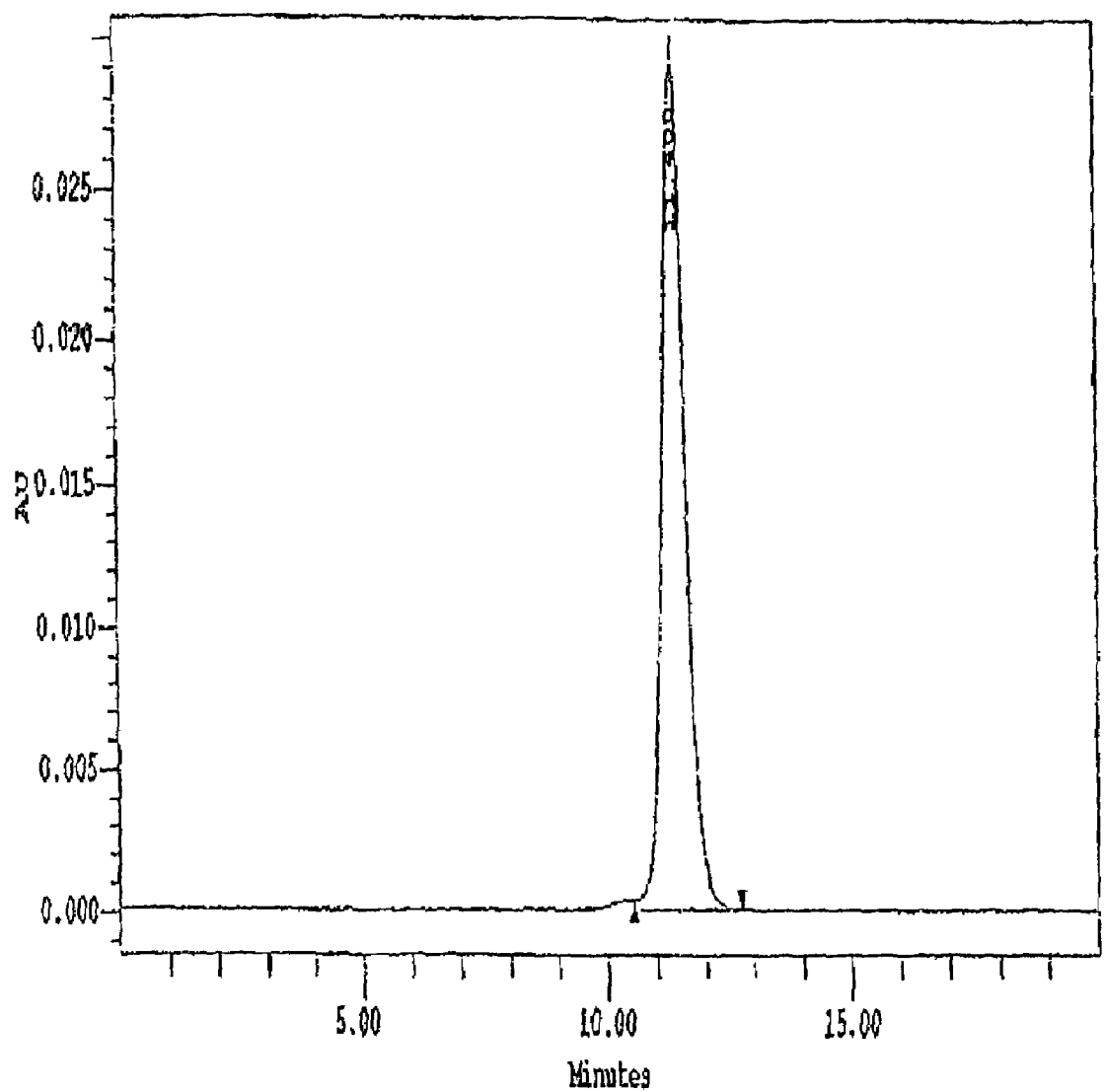
FIG. 5 shows the result of analyzing the purity of the purified modified toxin with RP-HPLC.
Figure 6:
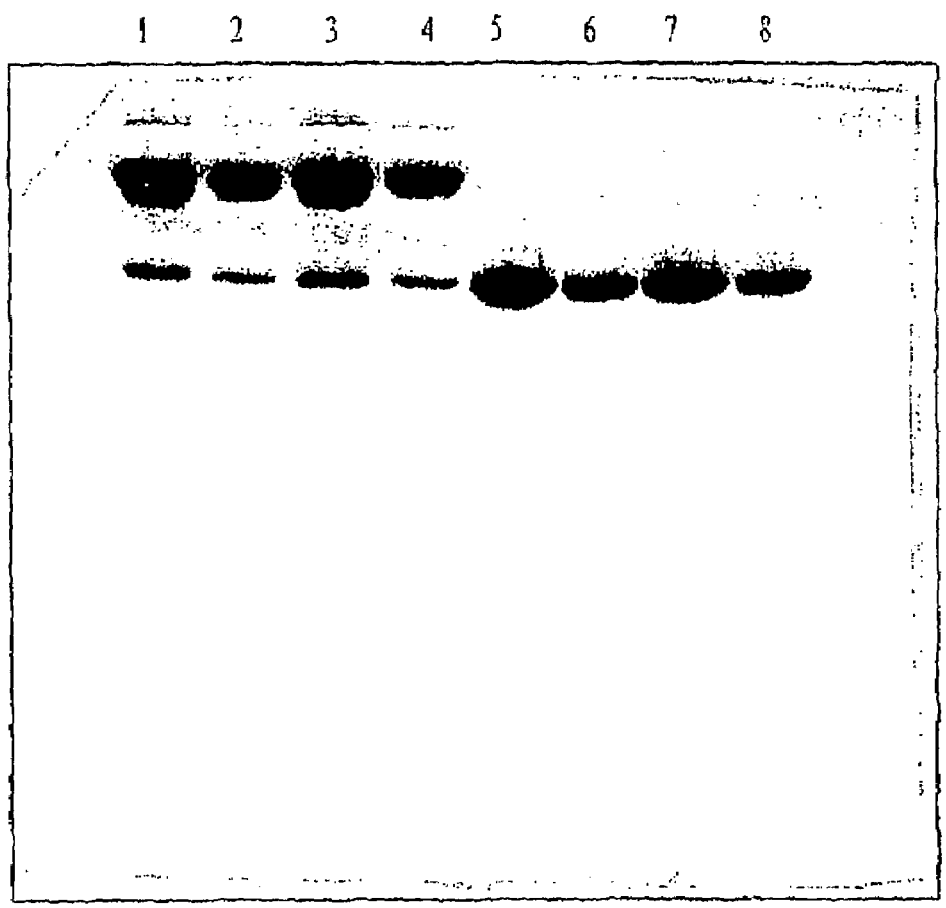
FIG. 6 shows the results of analyzing and comparing the formations of multiple structures in the original modified toxin that is purified according to the method as shown in FIG. 3 from *E. coli* which is transformed with the expression vector prepared according to the method as shown in FIG. 1, and in the modified toxin whose amino acid sequence is substituted, that is transformed with the expression vector prepared according to the method as shown in FIG. 2 and is purified according to the method as shown in FIG. 3.

The resulting concentrate was passed through a cation exchange column, a CM-SEPHAROSE™ column that was equilibrated with 10 mM Tris buffer (pH 6.5), and then it was washed twice with a 10 mM Tris buffer solution (pH 6.5) and with a 10 mM Tris buffer solution (pH 8.0). The elution from the column was conducted with 0–200 mM of a NaCl linear gradient. The collected fractions were passed through an anion exchange DEAD-SEPHAROSE™) column that was equilibrated with a 10 mM Tris buffer solution (pH 8.0) to collect the flowthrown fraction. 5 times diafiltration was performed. The collected flowthrown fraction was concentrated with an ultra-filtration membrane with a pore size of 10 kDa, and was diluted with PBS (phosphate buffer saline) and reconcentrated to obtain the final purified liquid. FIG. 3 shows this process for purifying SEC-SER modified toxin protein as a non-reducing SDS-PAGE.

Figure 2:
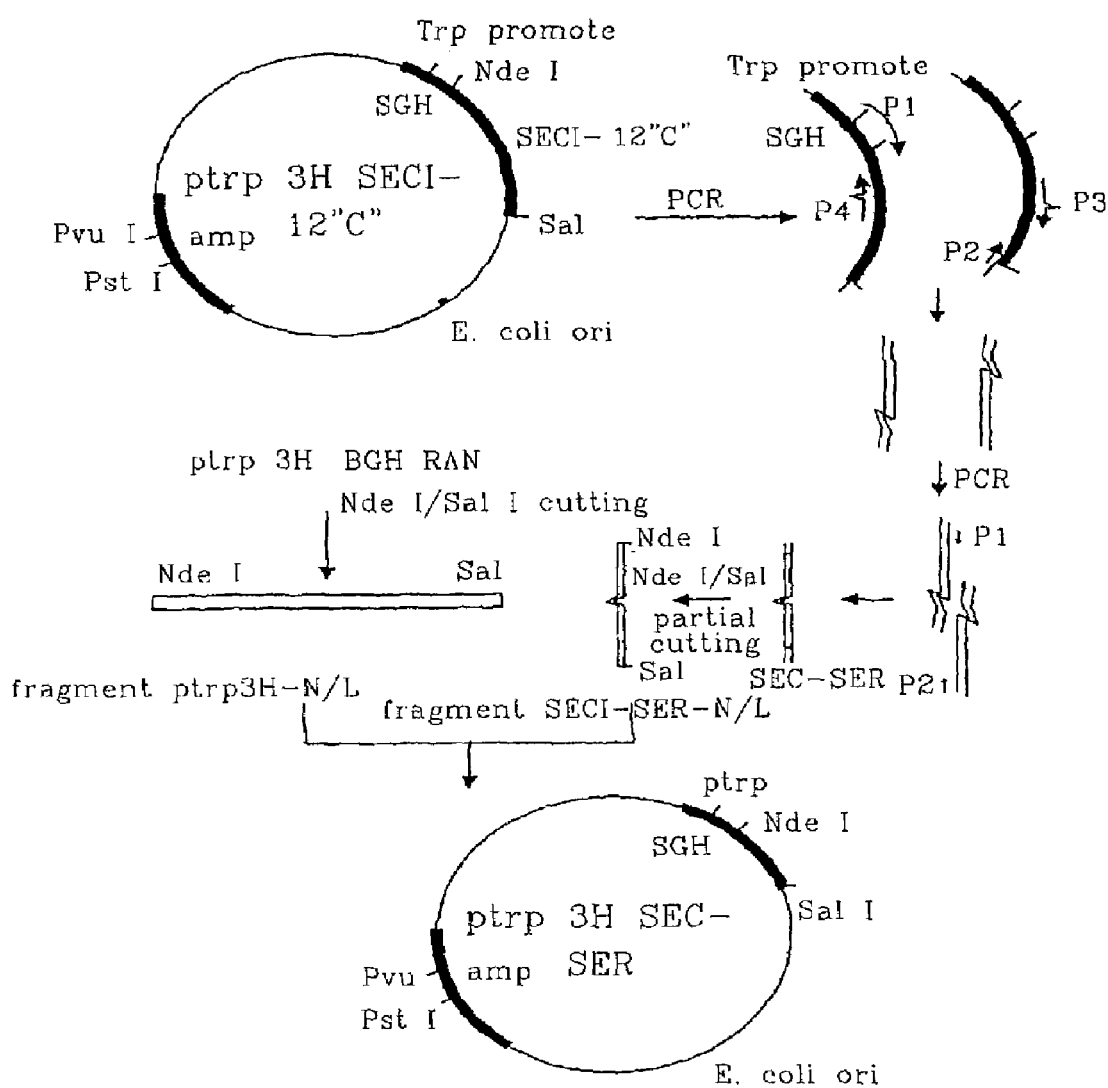
FIG. 2 shows a method for producing an expression vector by substituting the 95th cysteine codon in the genes of a modified toxin with the serine codon in the vector prepared in accordance with the method as shown in FIG. 1.
Figure 7A:
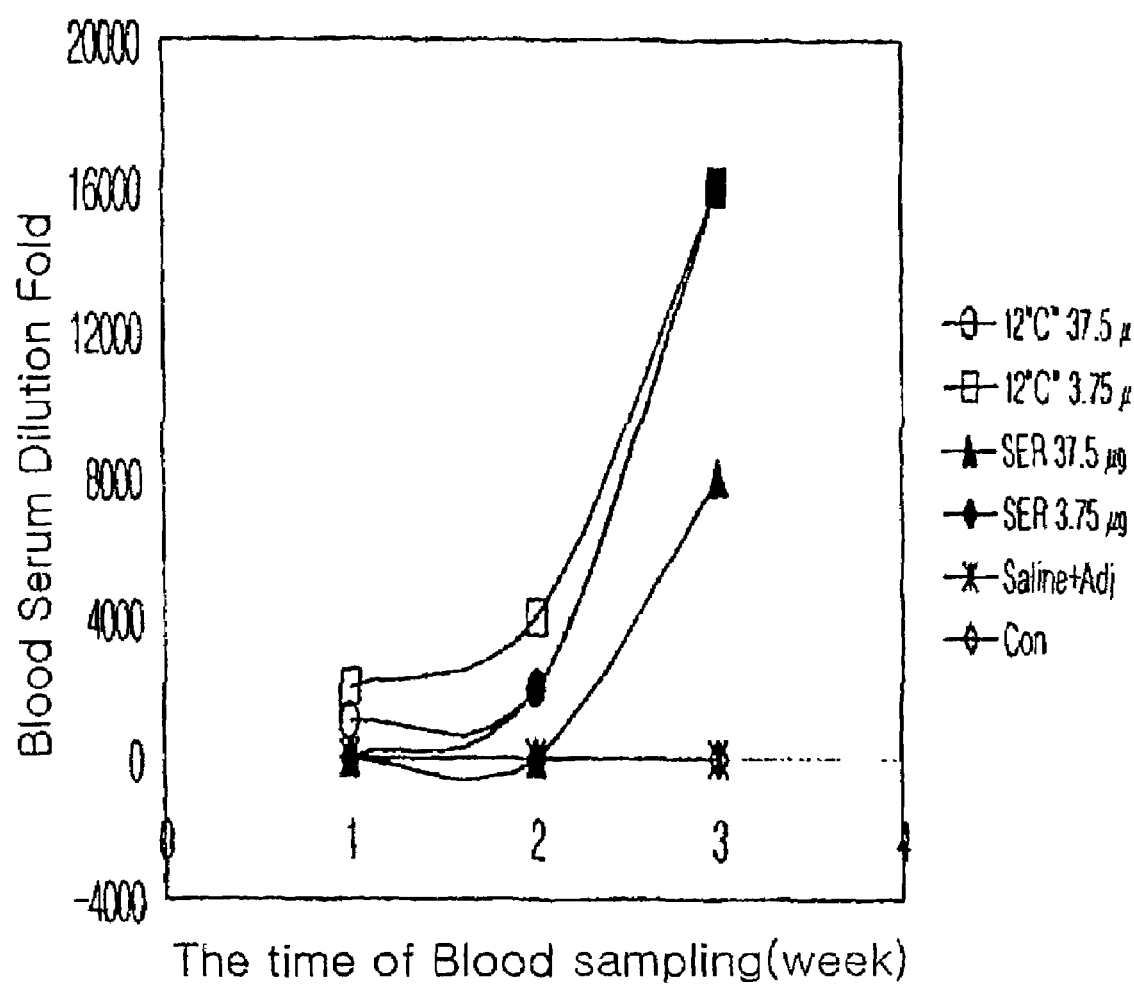
FIGS. 7A to 7C show the results of measuring the antibody titer and the amount of cytokine production according to the dose of modified toxin in mice.
Figure 7B:
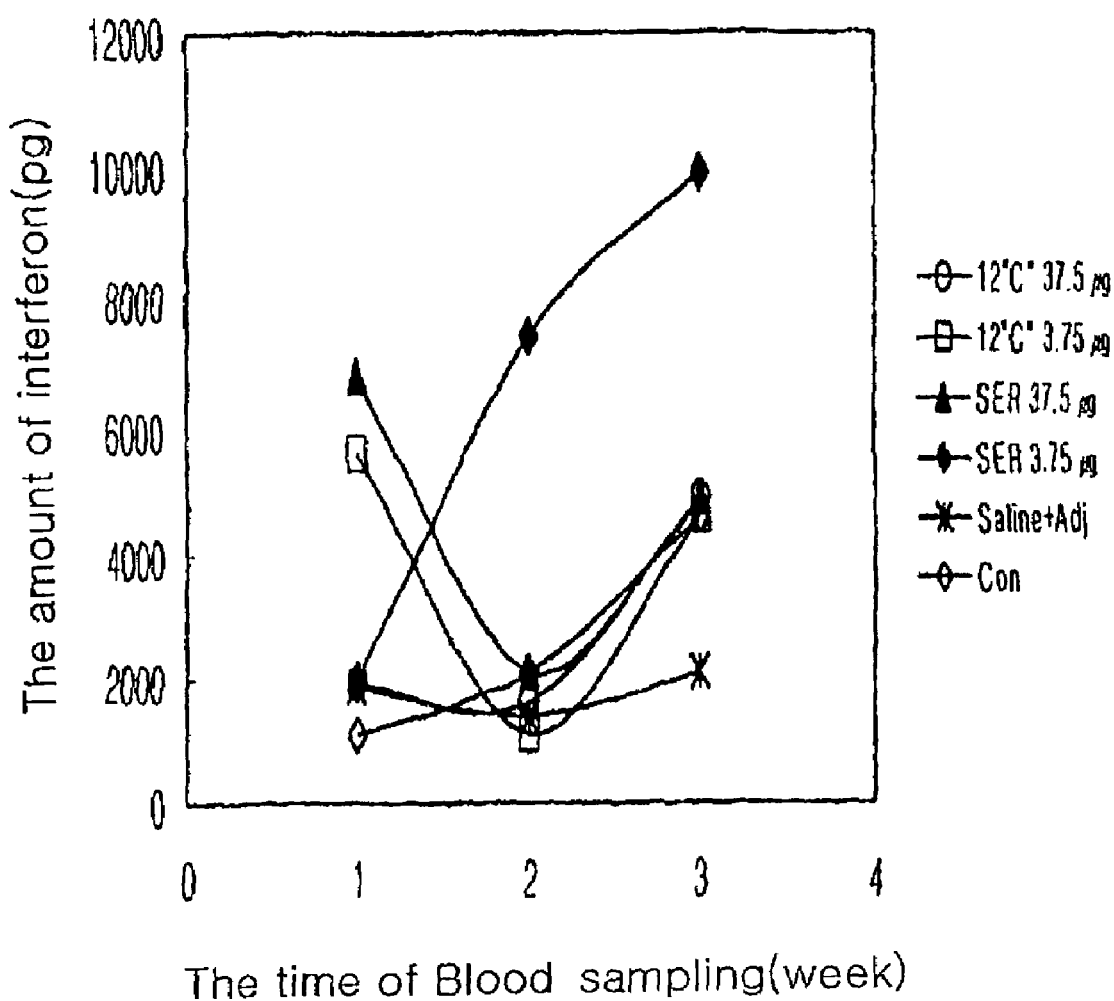
Figure 7C:
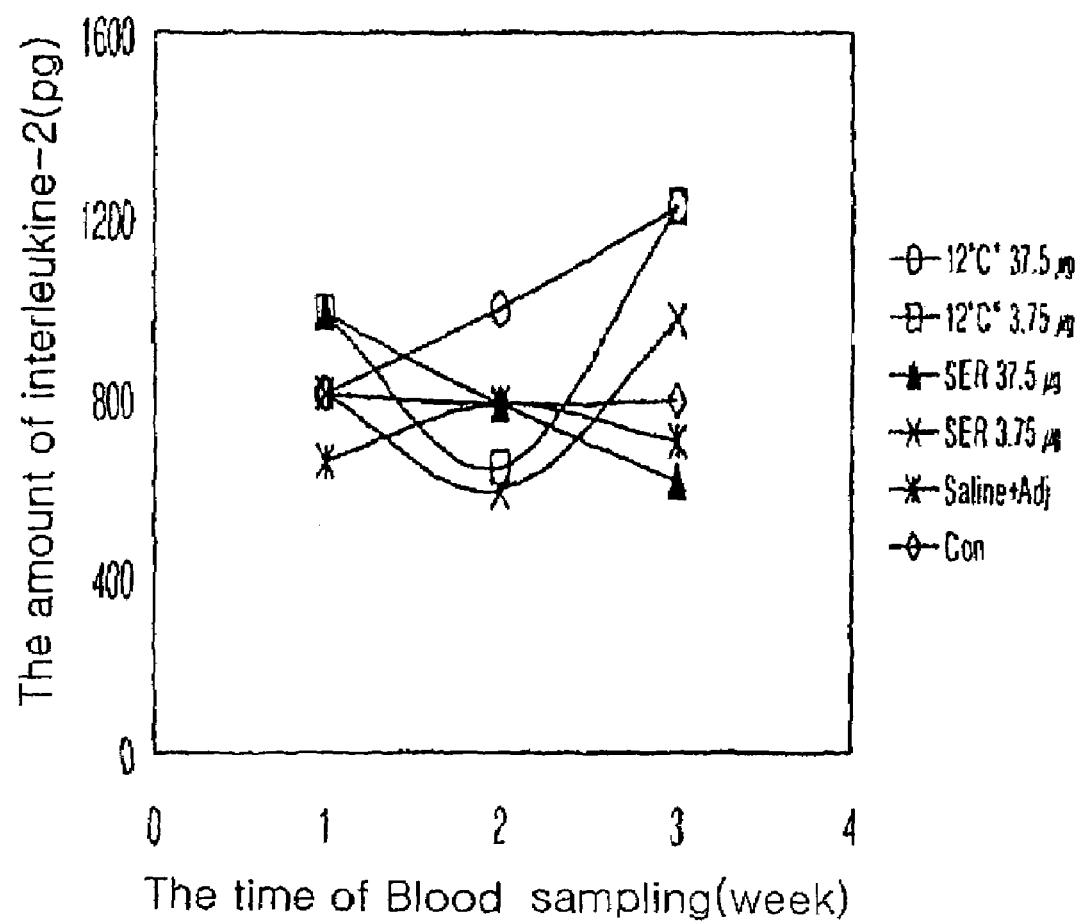

The first row shows the expression of SEC-SER modified toxin protein in *E. coli*, the second row shows the step before passing through the CM-SEPHAROSE™ column, the third row shows the final protein liquid which was purified with the CM-SEPHAROSE™ column and DEAD-SEPHAROSE™ column and then the buffer solution was exchanged with PBS, and the fourth row shows that the standard molecular weight marker proteins and the molecular weight of purified toxin protein were identified as approximately 28 kDa.

FIGS. 4-1 to 4-11 shows the results of analyzing the N-terminal of the SEC-SER modified toxin protein as shown in the third row of FIG. 3. The amino acid sequence from residue 1 to residue 10 of N-terminal was identified as follows:

Met-Glu-Ser-Gln-Pro-Asp-Pro-Thr-Pro-Asp (residues 1–10, SEQ ID NO: 1)

This result proves that the purified protein corresponds to the protein expressed in Example 1. The sequencing of the protein was conducted using a Model 471A gas phase sequencer of ABI Company (Applied Bio systems Inc) using the Edman Degradation method.

FIG. 5 shows the result of analyzing the purity of protein shown in the third row of FIG. 3 with reverse phase HPLC, and this shows the purity to be 95% or more.

EXAMPLE 4

The Preparation of Mastitis Vaccine from SEC-SER Protein

In order to prepare the final solution, a phosphate buffer aqueous solution containing 2.16 mg/ml of dissolved recombinant SEC-SER protein was manufactured so that the concentration of protein amounted to 6% (w/w) of the total ingredients. The final solution was supplied to a spray drier (BUCHI 191) at the flow rate of 0.55 ml/min while spray drying it into micro particles. The temperature of the inlet for dry air was 70° C., and that of the outlet was 50° C. The size of the obtained micro particles was 0.1 to 5 μm in diameter.

[Test 1]

The Comparison of the Stabilities of SEC-12"C" Modified Protein and SEC-SER Protein In order to compare the degrees of the formations of multiple structures in SEC-SER protein of Example 1 purified according to Example 3 and in SEC1-12"C" of Comparative Example 1 purified from *E. coli* transformed with the expression vector ptrp 3H SEC1-12"C", both proteins were analyzed after storing in an 25° C. incubator for an extended period. In order to test the stabilities of SEC-12"C" of Comparative Example 1 and SEC-SER protein of Example 1, 1 mL of each protein in the form of solution was aseptically sprayed into a 5 mL vial, and some of these were freeze dried for comparison.

FIG. 6 shows the result of storing in an incubator at 25° C. for 6 months as a non-reductive SDS-PAGE.

The first and second rows show the conditions of SEC1-12"C" in the form of solution, the third and fourth rows show the conditions of SEC1-12"C" in the freeze dried form, the fifth and sixth rows show the conditions of SEC-SER in the form of solution, and the seventh and eighth rows show the conditions of SEC-SER in the freeze dried form.

The period of storage was from 0 hours to 6 months. In the case of SEC-12"C", the formation of dimer occurred from 0 hours. The difference between solution form and freeze-dried form was not significantly recognized. In the case of SEC-SER, namely when substituting the $95^{th}$ cysteine of SEC1-12"C" with serine, the formation of dimer did not occur, and the effect of the present invention is proven from this result.

[Test 2]

Test for Identifying Immunogen in the Animals to be Tested with Modified Toxin

In order to compare the immunogens of SEC-SER protein purified according to Example 3 and SEC1-12"C" purified according to the procedure of Example 3 from *E. coli* transformed with the expression vector ptrp 3H SEC1-12"C", modified toxins were suspended in PBS, and modified protein and an adjuvant, EMULSIGEN™ ISA-25, were mixed in the ratio of 3:1, and 3.75 μg/mouse and 37.5 μg/mouse were administrated to the test animals.

In order to identify the immunogen of the modified toxin, 156 mice (Balb/c, 4 weeks of age) were divided into 6 groups, and test vaccine was injected therein three times according to the scheme as described in Table 1, at the interval of 1 week, and then the antibody titer was measured and a cytokine analysis was conducted

TABLE 1

| Test Group | | Number of test animals | Dose (μl/ mouse | Blood sampling First | Second | Third |
|---|---|---|---|---|---|---|
| Comparative Example | I | 26 | 37.5 | 1 week | 2 weeks | 3 weeks |
| | II | 26 | 3.75 | 1 week | 2 weeks | 3 weeks |
| Example 1 | I | 26 | 37.5 | 1 week | 2 weeks | 3 weeks |
| | II | 26 | 3.75 | 1 week | 2 weeks | 3 weeks |
| Adjuvant | | 26 | Adjuvant | 1 week | 2 weeks | 3 weeks |
| Control | | 26 | PBS | 1 week | 2 weeks | 3 weeks |

FIG. 7-1 shows the antibody titer measurement results. The antibody titer was not recognized before injection, but both in SEC1-12"C" and SEC-SER modified toxin, the antibody titer begins to increase one week after the first injection and remarkably increases after second injection.

FIGS. 7-2 and 7-3 show the capacity of cytokine formation. In the groups to which 3.75 μg of SEC-SER modified toxin was administrated, the capacity of γ-interferon production increases two weeks after the first injection, and reaches its peak at three weeks. In addition, in the groups to which SEC1-12"C" was administrated, the capacity of interleukine-2 formation increased two weeks after the first injection and 1200-fold more titer was recognized at three weeks.

[Test 3]

Test for Identifying Immunogen in the Animals to be Tested with Modified Toxin

The immune increase effect was examined in cows to be tested with vaccine prepared from modified toxin SEC-SER. EMULSIGEN™ ISA-25 and CMC (carboxy methyl cellulose) were used as an adjuvant. The test animals were 25 cows, and the scheme for injection is described in Table 2.

TABLE 2

Test for identifying immunogenicity of modified toxin tested animals

| Test groups | Dosage form | Antigen capacity (mg/animal) | Number of animals | Vaccination scheme | | |
|---|---|---|---|---|---|---|
| | | | | First | Second | Third |
| I | ISA 25 | 4 | 5 | 0 days | 2 weeks | 6 weeks |
| II | CMC | 4 | 5 | 0 days | 2 weeks | 6 weeks |
| III | ISA 25 | 0.4 | 5 | 0 days | 2 weeks | 6 weeks |
| IV | CMC | 0.4 | 5 | 0 days | 2 weeks | 6 weeks |
| V | Control (CMC) | — | 5 | 0 days | 2 weeks | 6 weeks |
| Total | | | 25 | | | |

The blood was sampled at 0 days (first), 2 weeks (second), 6 weeks (third), 10 weeks (fourth) and 14 weeks (fifth).

Figure 8A:
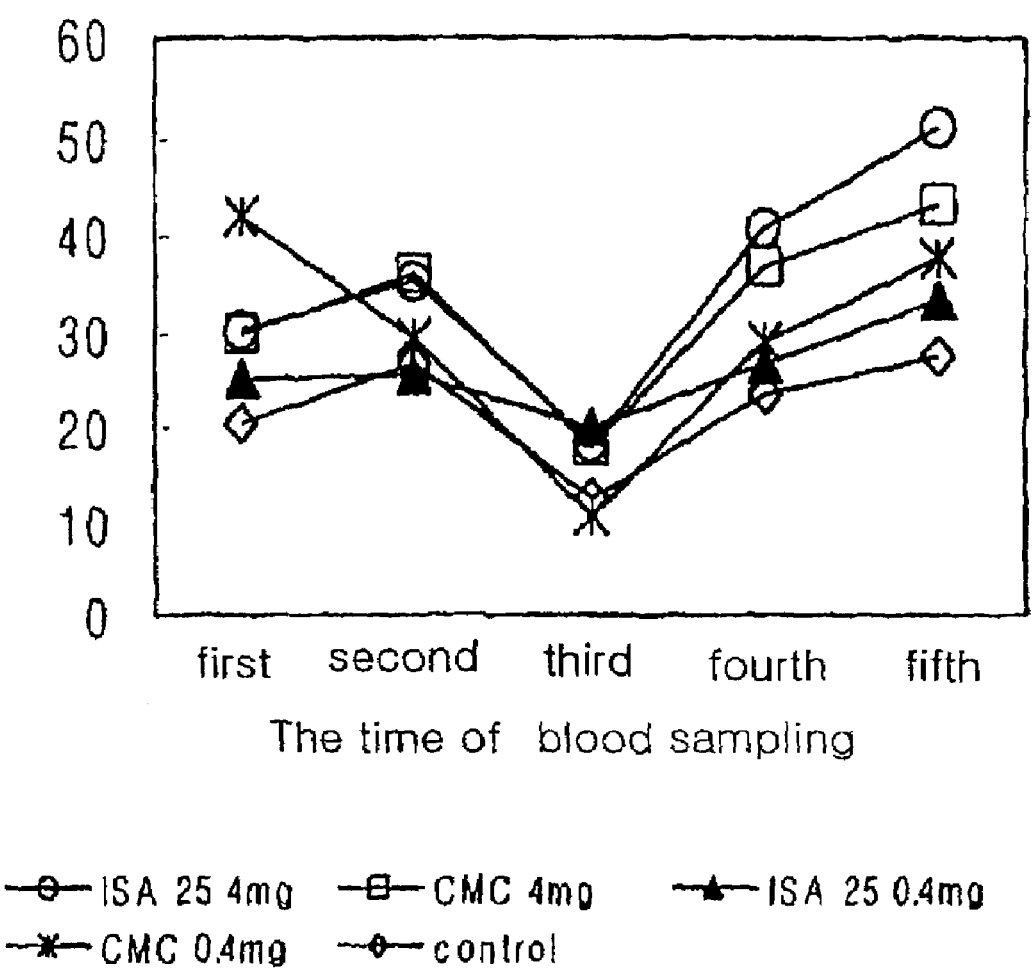
Figure 8C:
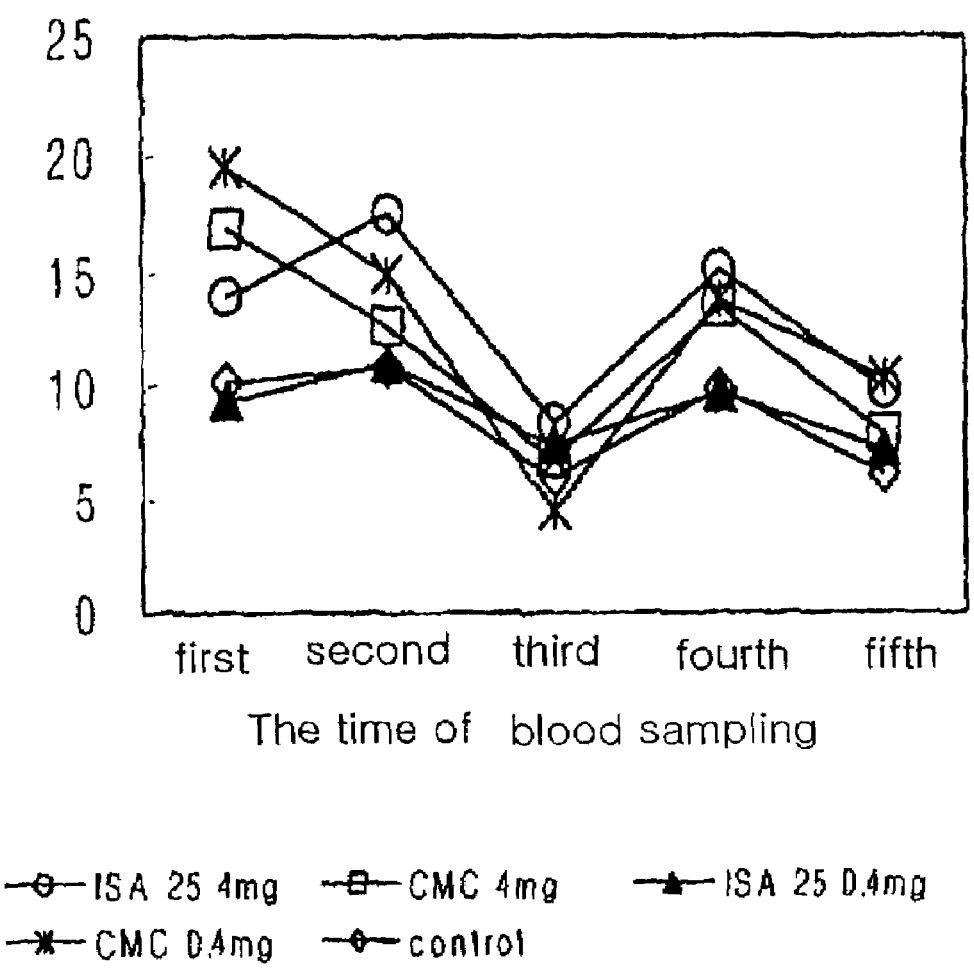

The change of the immune cells was as follows: The rates of total lymphocytes involved in the secondary immune response (CD2+), T lymphocytes such as T helper cells (CD4+), T cytotoxic/suppressor cells (CD8+), etc. and subgroup cells decrease until 6 weeks after the first injection (4 weeks after the second injection), and then they increase from the third injection, suggesting that, 14 weeks after the first injection, the continuous increase in the distribution of CD2+ T lymphocyte excepting CD8+ T lymphocyte was maintained and the humoral immune response occurred. In addition, the change of Non T/Non B shows a similar tendency in the change of CD2+M and CD4+ T lymphocyte, suggesting that the effective immunization occurred after the third injection. FIG. 8a shows the change of CD2+ T lymphocyte, FIG. 8b shows the change of CD4+ T lymphocyte, and FIG. 8c shows the change of CD8+ T lymphocyte.

Figure 8D:
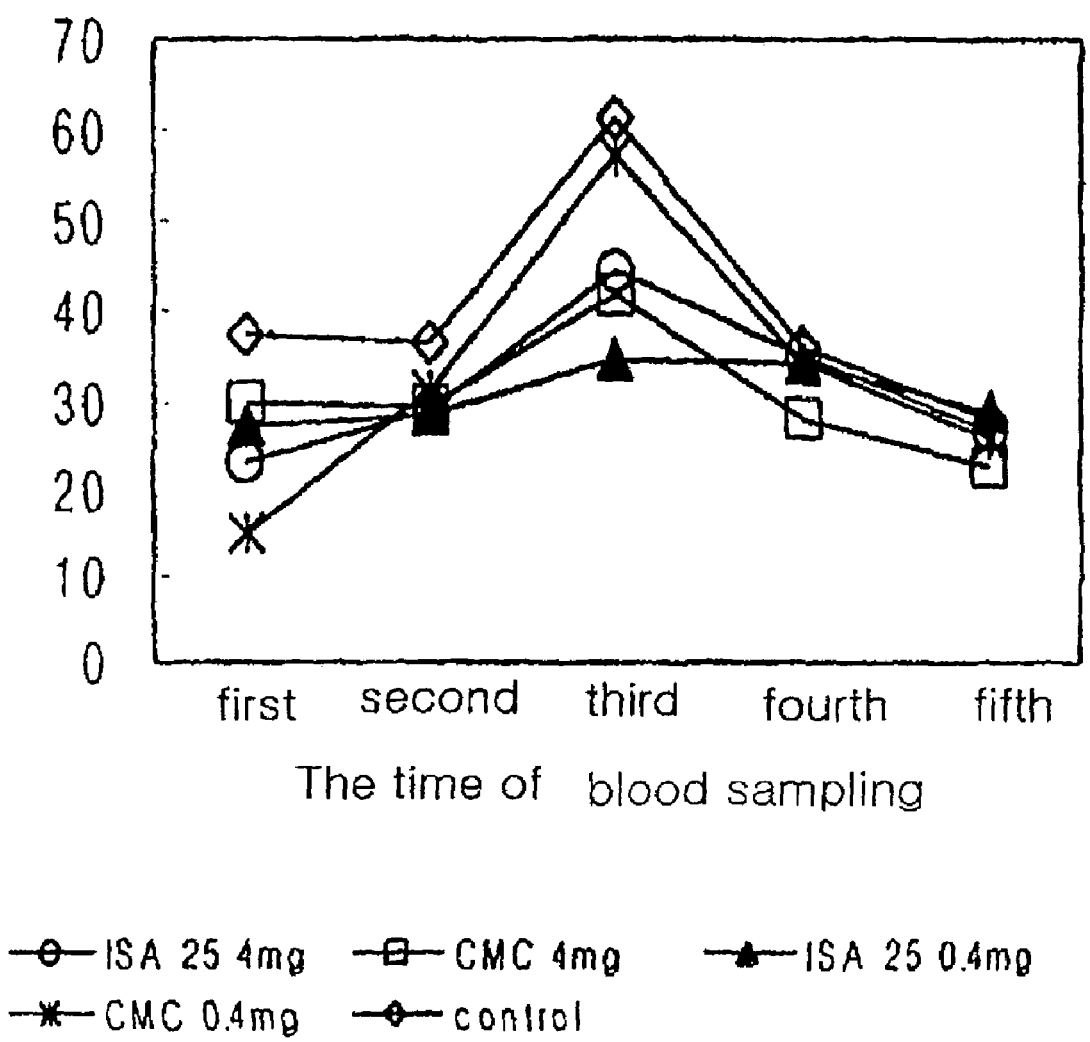
Figure 8F:
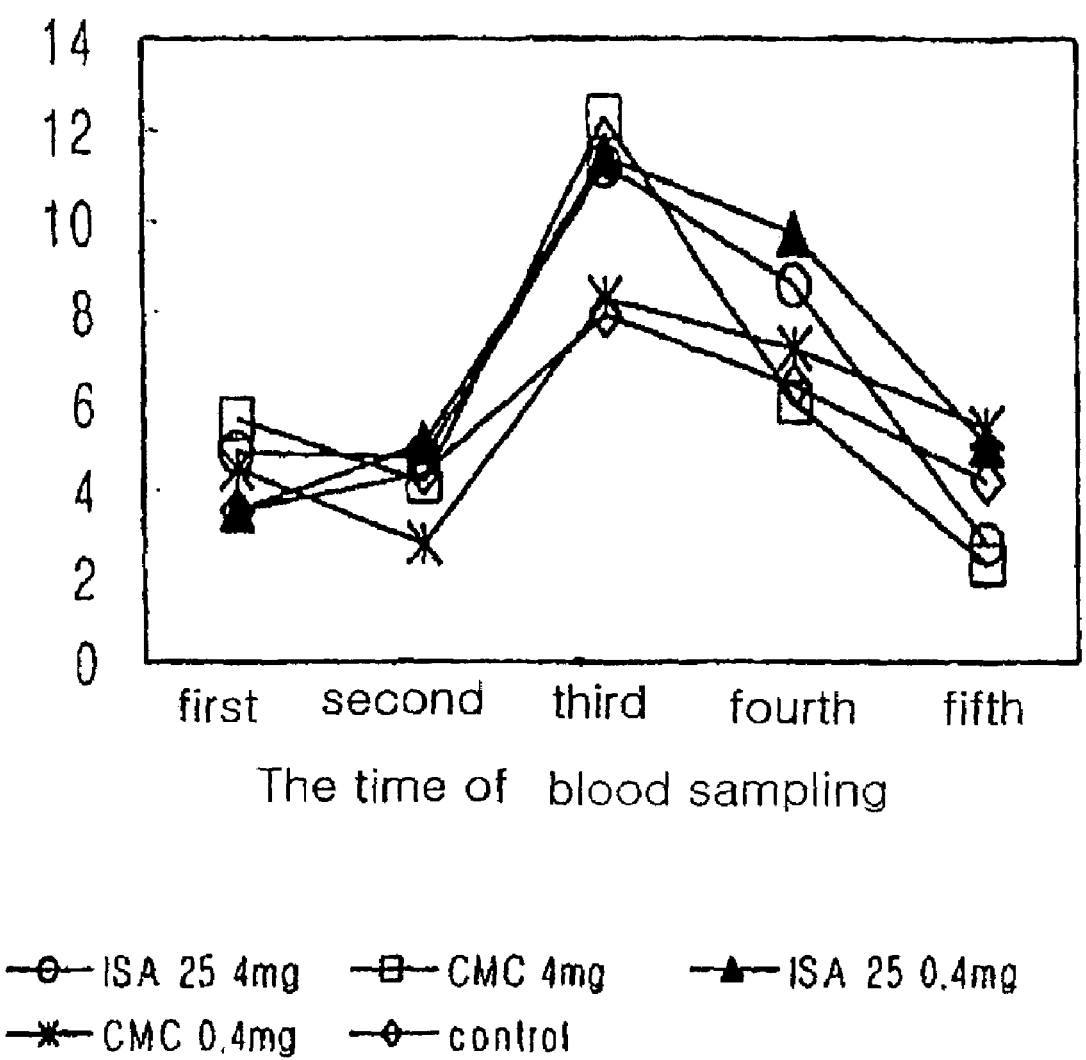

On the other hand, the distributions of B lymphocyte that plays a critical role in the production of monocytes and antibodies involved in the initial defense mechanism largely increase before the third injection (6 weeks after the first injection). Then, the distribution of B lymphocyte somewhat decreases, and the distribution of monocyte remarkably decreases and, 14 weeks after the first injection, it reaches a normal value nearly identical with the value before injection. The change in the distribution of MHC class II that is expressed by macrophage involved in primary immune response also shows this tendency. FIG. 8d shows the change in B lymphocyte, FIG. 8e shows the change in N lymphocyte, FIG. 8f shows the change in monocyte and FIG. 8g shows the change in MHC class II molecules.

The immune effect test was conducted according to the following method:

1) The Measurement of Antibody Titer (ELISA Method)

The modified toxin diluted with a coating buffer (NaCO3, 1.5 g, NaHCO3 2.93 g/1 L, pH 9.6) was introduced in 96 well flat bottom plate in an amount of 100 μl/well (5 μg/well) and it stood overnight at 4° C. Then it was washed with a cleaning buffer solution (PBST; NaCl 8 g, $KH_2PO_4$ 0.2 g, $NaHPO_4$ 0.87 g, KCl 0.2 g, TWEEN™ 20 0.5 g/1 L, pH 7.2), and then it was blocked with 100 μl of cleaning and buffer containing 1% BSA and 0.1% TWEEN™ 20 at 37° C. for 1 hour. After washing 2–3 times, mouse serum diluted to 1:2000 with EIA was introduced in each well in an amount of 100 μl/well and was reacted for 1 hour at 37° C. After washing 4–6 times, a substrate OPD was introduced in each well in an amount of 100 μl/well and reacted at room temperature for about 10 minutes, and then the absorbance was measured at 492 nm.

2) Blood Sampling and the Separation of Lymphocyte

The blood of mice was sampled and separated by a concentration gradient centrifugal method using FICOLL-HYAQUE™ (D=1.086; Lympholyte-M). The separated lymphocyte was washed with PBS three times, and it was calculated to be $1 \times 10^7$/ml and used for subsequent experiments.

3) The Examination of the Distribution of Subgroup of Immune Cell

The distribution of subgroups of immune cells was examined with a mouse-specific monoclonal antibody using a FACScan. 50 μl of each monoclonal antibody were introduced in each conical bottom microplate well, and 100 μl of 1×107/ml lymphocyte separated from the blood were respectively added thereto, the mixture was reduced at 4° C. for 30 minutes, and was then centrifuged with a 4° C. primary cleaning buffer (PBS 450 ml, ACD 50 ml, 20% $NaN_3$ 5 ml, gamma globuline free horse serum 10 ml, 250 Mm EDTA 20 ml, 0.5% phenol red 1 ml) at 2000 rpm for 3 minutes. Then the supernatant was removed and the lymphocyte pellet was resuspended with voltex mixer, and this step was repeated three times.

The cleaned pellet was washed again by diluting a FITC-conjugated goat anti-mouse IgG antibody (Catalog Lab Inc., San Francisco) in a secondary cleaning buffer (a primary cleaning buffer excluding horse serum), adding them to each well in an amount of 100 μl/well, reducing on ice for 30 minutes, and centrifuging it with the secondary cleaning buffer three times. Finally, a 2% PBS-formalin (35% formalin in 20 ml, PBS 980 ml) solution was added to each well in an amount of 200 μl/well and it was fixed, and then the differentiated cell of lymphocyte was analyzed with a FAC-Scan.

4) The Analysis of Cytokine Production

The cytokine production capacity was analyzed using a mouse cytokine ELISA kit. Specifically, the culture supernatant of the separated lymphocyte stimulated with ConA and the culture supernatant of the negative control were collected 4 days after culturing, and the capacity for producing gamma interferon and interleukine-2 was analyzed according to the process recommended by the manufacturer.

As shown in the above test, modified toxin SEC-SER in which the $95^{th}$ amino acid, cysteine, of a modified Staphylococcal toxin C1 was substituted with serine exhibits improved stability compared to the modified toxin of the prior art. It can therefore be used as an mastitis vaccine.

That is claimed is:

1. A stable purified Staphylococcal toxin SEC-SER, which is a modified Staphylococcal enterotoxin C1, and comprises the amino acid sequence of SEQ ID NO: 1.

2. An isolated modified gene fragment encoding the Staphylococcal toxin SEC-SER of claim 1 comprising the nucleotide sequence of SEQ ID NO: 2.

3. A ptrp 3H SEC-SER expression vector containing the gene fragment of claim 1.

4. An *E. coli* transformed with the expression vector of claim 3 and having the deposit number KCTC 0645BP.

5. A vaccine containing the Staphylococcal toxin SEC-SER according to claim 1.

6. The vaccine according to claim 5, wherein said vaccine is for administration to one or more kinds of animals selected from the group consisting of cows, pigs, horses, sheep, dogs and cats.

* * * * *

SEQUENCE LISTING

<160> NUMBER OF SEQ ID NOS: 6

<210> SEQ ID NO 1
<211> LENGTH: 228
<212> TYPE: PRT
<213> ORGANISM: Artificial Sequence
<220> FEATURE:
<223> OTHER INFORMATION: Staphylococcal enterotoxin SEC-SER

<400> SEQUENCE: 1

```
Met Glu Ser Gln Pro Asp Pro Thr Pro Asp Glu Leu His Lys Ala Ser
1               5                   10                  15

Lys Phe Thr Gly Leu Met Glu Asn Met Lys Val Leu Tyr Asp Asp His
            20                  25                  30

Tyr Val Ser Ala Thr Lys Val Lys Ser Val Asp Lys Phe Leu Ala His
        35                  40                  45

Asp Leu Ile Tyr Asn Ile Ser Asp Lys Lys Leu Lys Asn Tyr Asp Lys
    50                  55                  60

Val Lys Thr Glu Leu Leu Asn Glu Gly Leu Ala Lys Lys Tyr Lys Asp
65                  70                  75                  80

Glu Val Val Asp Val Tyr Gly Ser Asn Tyr Tyr Val Asn Cys Ser Gly
                85                  90                  95

Lys Thr Cys Met Tyr Gly Gly Ile Thr Lys His Glu Gly Asn His Phe
            100                 105                 110

Asp Asn Gly Asn Leu Gln Asn Val Leu Ile Arg Val Tyr Glu Asn Lys
        115                 120                 125

Arg Asn Thr Ile Ser Phe Glu Val Gln Thr Asp Lys Lys Ser Val Thr
    130                 135                 140

Ala Gln Glu Leu Asp Ile Lys Ala Arg Asn Phe Leu Ile Asn Lys Lys
145                 150                 155                 160

Asn Leu Tyr Glu Phe Asn Ser Ser Pro Tyr Glu Thr Gly Tyr Ile Lys
                165                 170                 175

Phe Ile Glu Asn Asn Gly Asn Thr Phe Trp Tyr Asp Met Met Pro Ala
            180                 185                 190

Pro Gly Asp Lys Phe Asp Gln Ser Lys Tyr Leu Met Met Tyr Asn Asp
        195                 200                 205

Asn Lys Thr Val Asp Ser Lys Ser Val Lys Ile Glu Val His Leu Thr
    210                 215                 220

Thr Lys Asn Gly
225
```

<210> SEQ ID NO 2
<211> LENGTH: 867
<212> TYPE: DNA
<213> ORGANISM: Artificial Sequence
<220> FEATURE:
<223> OTHER INFORMATION: Staphylococcal enterotoxin SEC-SER

<400> SEQUENCE: 2

| | | | | | |
|---|---|---|---|---|---|
| atggagagcc | aaccagaccc | tacgccagat | gagttgcaca | aagcgagtaa | attcactggt | 60 |
| ttgatggaaa | atatgaaagt | tttatatgat | gatcattatg | tatcagcaac | taaagttaag | 120 |
| tctgtagata | aatttttggc | acatgattta | atttataaca | ttagtgataa | aaaactgaaa | 180 |
| aattatgaca | aagtgaaaac | agagttatta | aatgaaggtt | tagcaaagaa | gtacaaagat | 240 |
| gaagtagttg | atgtgtatgg | atcaaattac | tatgtaaact | gctctggcaa | aacttgtatg | 300 |

```
tatggaggaa taacaaaaca tgaaggaaac cactttgata atgggaactt acaaaatgta      360
cttataagag tttatgaaaa taaaagaaac acaatttctt ttgaagtgca aactgataag      420
aaaagtgtaa cagctcaaga actagacata aaagctagga atttttttaat taataaaaaa    480 aatttgtatg agtttaacag ttcaccatat gaaacaggat atataaaatt tattgaaaat     540
aacggcaata cttttttggta tgatatgatg cctgcaccag gcgataagtt tgaccaatct    600
aaatatttaa tgatgtacaa cgacaataaa acggttgatt ctaaaagtgt gaagatagaa     660 gtccaccttca aacaaagaa tggataatgt taatccgatt ttgatataaa aagtgaaagt     720
attagatata tttgaaaggt aagtacttcg gtgcttgcct ttttaggatg catatatata     780
gattaaaccg cacttctata ttaatagaaa gtgcggttat ttatacactc aatctaaact     840
ataataattg gaatcatctt caaatag                                         867
```

<210> SEQ ID NO 3
<211> LENGTH: 90
<212> TYPE: DNA
<213> ORGANISM: Artificial Sequence
<220> FEATURE:
<223> OTHER INFORMATION: P1 Primer has a NdeI recognition site

<400> SEQUENCE: 3

```
ggaattccat atgatcgaaa atcagcgttt attcaacatt gcagtttcta gcatggagga     60
attataaatg gagagccaac cagaccctac                                      90
```

<210> SEQ ID NO 4
<211> LENGTH: 32
<212> TYPE: DNA
<213> ORGANISM: Artificial Sequence
<220> FEATURE:
<223> OTHER INFORMATION: P2 Primer included in the Sa/I recognition site
      at the end of the SEC1-12"C" gene

<400> SEQUENCE: 4

```
gaattgtcga cttatcgatt ctttgttgta ag                                   32
```

<210> SEQ ID NO 5
<211> LENGTH: 30
<212> TYPE: DNA
<213> ORGANISM: Artificial Sequence
<220> FEATURE:
<223> OTHER INFORMATION: P3 Primer designed in order to substitute the
      cystine codon that was substituted for the firstly removed site in
      SGH SEC1-12"C" with serine codon

<400> SEQUENCE: 5

```
aattactatg taaactgctc tggcaaaact                                      30
```

<210> SEQ ID NO 6
<211> LENGTH: 23
<212> TYPE: DNA
<213> ORGANISM: Artificial Sequence
<220> FEATURE:
<223> OTHER INFORMATION: P4 Primer designed in order to substitute the
      cystine codon that was substituted for the firstly removed site in
      SGH SEC1-12"C" with serine codon

<400> SEQUENCE: 6

```
gttttgccag agcagtttac ata                                             23
```